United States Patent
Nakajima

(10) Patent No.: US 6,411,945 B1
(45) Date of Patent: Jun. 25, 2002

(54) METHOD AND APPARATUS FOR DESIGNING MULTI-COMPONENT MATERIAL, OPTIMIZATION ANALYZER AND STORAGE MEDIUM USING LEARNING PROCESS

(75) Inventor: Yukio Nakajima, Tokyo (JP)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 09/051,416

(22) PCT Filed: Aug. 8, 1997

(86) PCT No.: PCT/JP97/02784

§ 371 (c)(1),
(2), (4) Date: Apr. 6, 1998

(87) PCT Pub. No.: WO98/06550

PCT Pub. Date: Feb. 19, 1998

(30) Foreign Application Priority Data

Aug. 8, 1996 (JP) ............................................. 8-210273

(51) Int. Cl.⁷ ............................ G06F 15/18; G06F 1/00
(52) U.S. Cl. ................................ 706/19; 703/1; 703/2; 703/8
(58) Field of Search ....................... 706/912, 19; 703/1, 703/2, 8

(56) References Cited

U.S. PATENT DOCUMENTS

| | | | | |
|---|---|---|---|---|
| 5,559,729 A | * | 9/1996 | Abe | 703/2 |
| 5,710,718 A | * | 1/1998 | Kamegawa et al. | 703/1 |
| 5,724,254 A | * | 3/1998 | Millett et al. | 702/179 |

FOREIGN PATENT DOCUMENTS

| | | |
|---|---|---|
| EP | 0 647 911 A2 | 4/1995 |
| JP | 6-248118 | 9/1994 |
| JP | 6-266441 | 9/1994 |
| JP | 7-210582 | 8/1995 |
| JP | 9-16654 | 1/1997 |
| WO | WO 94/16877 | 8/1994 |

OTHER PUBLICATIONS

Goldberg, David E., "Genetic Algorithm in Search, Optimization and Machine Learning", Addison–Wesley, 1989.*
Oda, Juhachi; Okada, Hiroyasu; "Design method of materials composed of some ingredients by using neural network"; Optimization Symposium '94; pp. 57–63, 1994.*
A formulation tool, Alan H. Bohl, *Chemtech*, May 1988 pp. 284–289.
The Role of Integrated A1 Technologies in Product Formulation, *ISA Transactions*, 1992, vol. 31, No. 2, pp. 151–157.
Design Method of Materials Composed of Some Ingredients by Using Neural Network, Juhachi Oda and Hiroyasu Okada, *Optimization Symposium '94*, pp. 57–62.
Non–Linear Multi–Variate Analysis—Approach by Neural Network, Hideki Toyota, *Asakura Book Store*, 1996, pp. 11–13 and 162–166.
Design and Analysis in Mixed Experiments, Manabu Iwasaki, *Scientist Co.*.

* cited by examiner

Primary Examiner—George B. Davis
(74) Attorney, Agent, or Firm—Sughrue Mion, PLLC

(57) ABSTRACT

In an optimization apparatus 30, a known compositional ratios and the like, and mechanical behaviors thereof are inputted by an experimental data input unit 40 and a learning is conducted in a non-linear calculation unit 32 in order to establish a corresponding relation between compositional ratios of multi-component materials and the like, and mechanical behaviors thereof as a conversion system based on a neural network. Compositional ratios and the like are inputted in an optimization item input unit 42, and a mechanical behaviors are predicted in an optimization calculation unit 34 from compositional ratios and the like of the multi-component materials using the optimization item and the conversion system of the calculation unit 32, and an objective function is optimized until the objective function, expressing the mechanical behaviors are converged.

19 Claims, 14 Drawing Sheets

(a)

(b)

(a)

(b)

METHOD AND APPARATUS FOR DESIGNING MULTI-COMPONENT MATERIAL, OPTIMIZATION ANALYZER AND STORAGE MEDIUM USING LEARNING PROCESS

FIELD OF THE INVENTION

The present invention relates to a design method, an optimization analyzing apparatus and a storage medium having a stored optimization analyzing program for a multi-component material and more particularly, to a design method, an optimization analyzing apparatus and a storage medium having a stored optimization analyzing program for design of a multi-component material composed of many components, for example design of a rubber compound for a tire.

BACKGROUND ART

Material design is to determine compositional ratios of components for a material to obtain the material having target mechanical behaviors, production conditions therefor and the like. The mechanical behaviors include physical quantities, such as physical properties of a material itself, sizes thereof and the like.

A conventional material design has mainly been conducted through experiences or trial and error and there has been difficulty in designing a material in the case of a material composed of three or more components. For example, in designing a rubber member for producing a tire, since various physical properties are considered, there have generally been taken procedures that a plurality of component materials having known physical properties are selected beforehand, the rubber member including predetermined compositions of respective component materials are as trial produced for tests and such tests are repeated until the member showing target performances in terms of a Young's modulus and the like is achieved. In this manner, the rubber member is designed and developed.

There has been proposed a material design method in which compositional ratio of multi-component materials can automatically be determined with use of a hierarchical neural network, if material properties are designated (see "Design Method for Multi-component Material Using Neural Network" in the papers presented at the first symposium on optimization sponsored by Japan Society of Mechanical Engineers, pp. 57–62).

In this method, however, if it is tried to determine compositional ratio of components by inputting material properties, which are slightly different from ones of an actual material, negative compositional ratio of the material is output, that is, compositional ratio of components with which a material cannot actually be composed is obtained and thus there arises a case where obtained compositional ratio cannot be used. Further, mechanical behaviors, such as material properties, except for mechanical behaviors which can be obtained the target performances cannot meet requirements from the market, so that the method has in fact been unable to apply in many practical aspects.

Another method has been known in which a polynominal is assumed for correlating compositional ratios of multi-component materials composed of a plurality of components and production conditions with mechanical behaviors of the materials and a calculating means determining coefficients of the polynominal by method of least squares and optimization are combined to each other (see authored by Manabu Iwasaki, "Planning and Analysis in Mixed Experiments" published by Scientist Co.,).

In this method, however, when optionality enters in assuming the polynominal or the number of the multi-component materials is three or more, the assumption of the polyniminal becomes difficult and the correlating cannot be performed with a high accuracy. For this reason, a plan of material design obtained has not been useful.

In view of the above facts, it is an object of the present invention to provide an optimization analyzing apparatus for a multi-component material and a design method therefor, in which a design of a material composed of a plurality of components is facilitated and since optimization is conducted while constraint conditions are considered, a design range of compositional ratios of components of multi-component materials and a desired range of a mechanical behavior can in advance be set.

DISCLOSURE OF THE INVENTION

The present inventor has studied various aspects in order to achieve the above mentioned object and as a result, has paid attention to application of a non-linear prediction technique, for example, a neural network, in which a neural circuit network of a higher animal is modeled in an engineering manner, and optimization design approach, both the technique and the approach being utilizing in some fields except for a material design field, to a special field of material design, carried out a research and established a design method in which mechanical behaviors, such as a Young's modulus, are considered in a concrete manner.

A design method for a multi-component material of the present invention comprises the steps of: (a) determining a conversion system in which a non-linear correspondence between compositional ratios of multi-component materials composed of a plurality of components and mechanical behaviors of the multi-component materials is established; (b) determining an objective function expressing the mechanical behaviors and setting a constraint condition constraining an allowable range of at least one of the mechanical behaviors and the compositional ratios of the multi-component materials; and (c) determining a compositional ratio of the multi-component materials which gives an optimal solution of the objective function on the basis of the objective function and the constraint condition by using the conversion system determined in the step (a) to design a multi-component material based upon the compositional ratio of the multi-component materials determined.

The mechanical behaviors of the multi-component materials composed of the plurality of components, such as Young's modulus, tan δ and the like in a rubber member, are determined by the compositional ratios of components thereof. However, there are many cases where the mechanical behaviors are not changed in a linear manner, even though the compositional ratios are changed linearly. Therefore, in the step (a) of the present invention, the conversion system establishing a correspondence between the compositional ratios and the mechanical behaviors including a non-linear correspondence therebetween in advance is determined in advance. This conversion system can be determined with use of a non-linear prediction technique in which such a neural circuit network as neural network is modeled by an engineering approach.

In the step (b), the objective function expressing the mechanical behaviors is determined and the constraint condition constraining the allowable range of at least one of the mechanical behaviors and the compositional ratios of the multi-component materials is determined. As the objective function expressing mechanical behaviors, for example, a physical quantity governing excellency of a rubber member, such as a Young's modulus, tan δ and the like can be used. As the constraint constraining the allowable range of at least one of the mechanical behaviors and the compositional ratio of the multi-component materials, there are in a rubber member, for example, constraints for a Young's modulus and Poison's ratio of the rubber member and a constraint for a mass of at least one component of the multi-component materials. The objective function, design variable and constraint condition are not limited to the above mentioned but various kinds can be determined according to a design object of a tire.

In the step (c), the compositional ratio of the multi-component materials which give an optimal solution of the objective function is determined based on the objective function and the constraint condition by using the conversion system determined in the step (a) and then the multi-component material is designed on the basis of the compositional ratio of the multi-component materials thus determined. In this manner, the conversion system is determined so as to establish the non-linear correspondence between the compositional ratios of components of the multi-component materials composed of a plurality of components and the mechanical behaviors of the multi-component materials and then according to the conversion system a mutual relation is found between the compositional ratios of a plurality of components included in the materials and the mechanical behaviors thereof. Therefore, a multi-component material can be designed with a high precision and a lesser optionality by designing a multi-component material based on compositional ratios of the multi-component materials after the compositional ratio which give an optimal solution of the objective function is obtained. In the step (c), a value(s) of a design variable(s) which gives an optimal solution of the objective function can be obtained while the constraint condition is considered.

In the case where a multi-component material is designed in the step (c), the compositional ratio of the multi-component materials is set as a design variable, the value of the design variable which gives and optimal solution of the objective function is determined by using the conversion system determined in the step (a) while considering the constraint condition, and the multi-component material can be designed based on the design variable which gives the optimal solution of the objective function. In such a manner, if the constraint condition is considered, the allowable range of at least one of the mechanical behaviors and the compositional ratio of the multi-component materials can be considered and thereby not only can a range of a material design be defined in advance but a desired range thereof can also be set.

In the case where the value of the design variable is obtained in the step (c), a changed quantity of the design variable which gives the optimal solution of the objective function is predicted, while considering the constraint condition, based on a sensitivity of the objective function which is a ratio of a changed quantity of the objective function to a unit change quantity of the design variable and a sensitivity of the constraint condition which is a ratio of a changed quantity of the constraint condition to a unit change quantity in the design variable, and a value of the objective function obtained when the design variable is changed in a corresponding manner to a predicted quantity and a value of the constraint condition obtained when the design variable is changed in a corresponding manner to a predicted quantity are calculated so that a value of the design variable which gives the optimal solution of the objective function is effectively obtained by using the conversion system determined in the step (a) based on the predicted and calculated values while considering the constraint condition. Thereby, the value of the design variable which gives the optimal solution of the objective function under consideration of the constraint condition can be obtained. Then, a multi-component material can be designed by modifying compositional ratio or the like based on the design variable which gives the optimal solution of the objective function.

It has been known that to obtain an optimal solution in a general optimization approach is analogous to climbing a mountain. In this case, the optimal solution corresponds to the peak of the mountain if a height of the mountain is related with a performance or the like. Therefore, when the objective function is simple, since a design space is a shape like a mountain as shown on FIG. 8, the optimal solution can be obtained by an optimization approach which is based on a mathematical programming. Description will roughly be given on a design of a multi-component material using a typical drawing in FIG. 8 as a model, in which mountain climbing is used for illustration of optimization. The conversion system defines a non-linear correspondence between compositional ratios of the multi-component materials and mechanical behaviors of the multi-component materials. The conversion system is shown to be at a level (as a contour) in the design space (in the shape like a mountain). That is, there is a case where mechanical behaviors of multi-component materials are correlated with a plurality of compositional ratios of the multi-component materials and generally as the mechanical behavior approaches an optimal solution, the ranges of the compositional ratios are smaller as is a contour. The ranges of the compositional ratios of the multi-component materials are, in general limited by constraints in design and an actually allowable range, so that a relation between the mechanical behaviors and the compositional ratios of the multi-component materials can be restrained by a fence along a ridge of the mountain, as shown in FIG. 8. If the fence is assumed as constraint conditions, the relationship is considered to climb the mountain as shown in FIG. 8 with the help of an optimization approach, such as a mathematical programming or the like up to the peak of the mountain where an optimal solution can be obtained for the objective function in such a manner that the relationship is kept from going over to the outside of the fence by changing the design variable within the conversion system.

Besides, the constraint conditions (the fence) are effective for a guide in climbing a mountain in an optimization approach in addition to setting desired ranges of design of the compositional ratios of the multi-component materials and of the mechanical behaviors. That is, without a constraint condition, not only is a time for calculation increased but the calculation is not converged and furthermore the calculation is departed from the desired design range of the compositional ratio of the multi-component materials and the desired range of the mechanical behaviors.

In the present invention, when an optimal solution is obtained by the steps (a) to (c), execution of the following steps of (d) to (f) is indispensable to obtain the optimal solution. In more detail, the step (c) can comprises the steps of: (d) selecting as a design variable one compositional ratio of the multi-component materials included in the conversion system determined in the step (a); (e) changing a value of the design variable selected in the conversion system determined in the step (a) until an optimal solution of the objective function is given by using the conversion system determined in the step (a) while considering the constraint condition; and (f) designing the multi-component material based on the compositional ratio of the multi-component materials according to the design variable which gives the optimal solution of the objective function. In the step (d), the one compositional ratio of the multi-component materials included in the conversion system in the step (a) is selected as the design variable. In the next step (e), the design value to be selected in the conversion system is changed until an optimal solution of the objective function is given by using the conversion system determined in the step (a) while considering the constraint condition. Thereby, the design value changes subtly or gradually to obtain a optimal solution of the objective function. In the step (f), the multi-component material is designed based on the compositional ratio according to the design variable which gives an optimal solution of the objective function. In such a manner, since the one compositional ratio of the multi-component materials included in a conversion is selected as the design variable and the design variable to be selected is changed in the conversion system while considering the constraint condition until an optimal solution of the objective function is obtained, without beforehand preparation for a value of the design variable which gives the optimal solution of the objective function, a design value, which is close to a desired value of the design variable, may be selected in the conversion system and thereby a design of the multi-component material can be practiced with a high precision and a lesser optionality.

In this case, in the step (b), the constraint condition, in which an allowable range of at least one of the mechanical behaviors other than the determined objective function and the compositional ratios of the multi-component materials is constrained can be determined. In such a manner, the mechanical behaviors other than the objective function as a constraining allowable range can be used by determining the constraint condition, in which an allowable range of at least one of the mechanical behaviors other than the determined objective function and the compositional ratios of the multi-component materials is constrained.

In the step (e), a change in the design variable which gives an optimal solution of the objective function is predicted while considering the constraint condition based on a sensitivity of the objective function which is a ratio of a changed quantity of the objective function to a unit change quantity of the design variable and a sensitivity of the constraint which is a ratio of a changed quantity of the constraint condition to a unit change quantity of the design variable, and a value of the objective function obtained when the design variable is changed in a corresponding manner to a predicted quantity and a value of the constraint condition obtained when the design variable is changed in a corresponding manner to a predicted quantity are calculated. Besides, a value of the design variable can be changed until the value of the design variable gives an optimal solution of the objective function by using the conversion system determined in the step (a) based on the predicted and calculated values while considering the constraint condition. Thereby a value of the design variable can be obtained with ease during an optimal solution of the objective function is given by calculating a value of the objective function obtained when a value of a design variable is changed in a corresponding manner to a predicted quantity and a value of the constraint obtained when a value of a design variable is changed in a corresponding manner to a predicted quantity.

The present inventors has established a definite design method for a multi-component material after various studies by achieving an idea that a genetic algorithmic approach which is utilized in a field from that of the invention is applied to a special field of material design.

According to a design method of a multi-component material of the present invention, the step (c) comprises the steps of: define the compositional ratios of the multi-component materials in the conversion system determined in the step (a) as material base models to determine groups for selection including a plurality of material base models; determining the objective function, a design variable, a constraint and an adaptive function which can be evaluated from the objective function, for each material base model of the groups for selection; selecting two material base models from the groups for selection; conducting at least one of producing new material base models by cross overing design variables of the two material base models, at a predetermined probability with each other, and producing new material base models by modifying in part the design variables of at least one of the two material base models; changing the design variables of the new material base models produced to obtain an objective function, a constraint and an adaptive function of the new material base models produced by using the conversion system determined in the step (a); storing the material base models whose design variables have been changed and the material base models whose design variables have not been changed; repeating the storing steps until the number of the stored material base models reaches a predetermined number; determining whether or not new groups comprising the stored material base models of the predetermined number satisfies a predetermined convergence condition; wherein if not, the new groups are defined as the groups for selection and the above steps are repeated until the new groups satisfy the predetermined convergence condition; and if the predetermined convergence condition is satisfied, designing a multi-component material based on the compositional ratio of the multi-component materials obtained by the design variable which gives an optimal solution of the objective function from the predetermined number of the stored material base models by using the conversion system determined in the step (a) while considering the constraint condition.

In the step (a) the conversion system can be constructed with data in a multi-layered feed forward type neural network which has learned so as to convert the compositional ratios of the multi-component materials to the mechanical behaviors thereof.

As mentioned above, there are: a mathematical programming, a genetic algorithm and the like in a general optimization approach, and obtaining an optimal solution is understood to be analogous to climbing a mountain. At this point, since a height of the mountain is related to a performance or the like, the optimal solution corresponds to the peak of the mountain. In the case where an objective function is simple, a design space thereof (a mountain shape) is like Mt. Fuji having one peak as shown in FIG. 8, the optimal solution can be obtained an optimization approach based on a mathematical programming. However, when an objective function is more complex, a design space has a plurality of peaks, as shown in FIG. 9, an optimal solution cannot be obtained by the optimization approach based on a mathematical programming. The reason is that the optimization approach based on a mathematical programming recognizes a peak which is first reached by chance as an optimum solution among the plurality of peaks. A genetic algorithm has been proposed in order to solve this problem, but it requires tremendous amounts of experiments and computational time and sometimes calculation has not been converged. A neural network which can be used in the step (a) can be expected to have a prediction and a decision, both with higher precision than a linear transformation multi-variable analysis, a learning of a correlating a plurality of input data can be effected and thereby any function can be converted to approximation with any precision if the number of units in an intermediate layer is increased and besides the analysis has an advantage that it is excellent in extrapolation (see a book authored by Hideki Toyota "Non-Linear Multi-Variate Analysis—Approach by Neural Network" p. 11 to 13, p. 162 to 166, published by Asakura Book Store in 1996). This conversion system can be determined by use of a non-linear prediction technique in which a neural circuit network such as a neural network is modeled in an engineering way.

An optimal solution can be obtained by applying the neural network in a combination with the above mentioned optimization approach in a limited time, even when the objective function becomes complex.

In the case where design and development are conducted based on a design method of the present invention, it is made possible to conduct jobs of a design of a multi-component material having best mechanical behaviors to a performance evaluation of the multi-component material, mechanical behaviors can be achieved from in a mainly by a computer calculation which is different from a conventional design development in which trial and error are fundamental. Therefore conspicuous increase in efficiency is achieved and development costs can be decreased.

If a rubber compound is formed on the basis of a compositional ratio of multi-component materials designed by according to the above mentioned design method of a multi-component material, which mean that the rubber compound formed is constituted from respective components of multi-component materials having best mechanical behaviors. Accordingly, such a mixing contents as a quantity of carbon (% by weight), a quantity of a rubber chemical (% by weight) and the like can directly be determined according to applied conditions such as a production condition and a cost.

The above design method for a multi-component material can be realized by an optimization analyzing apparatus comprising; a conversion system calculating means for obtaining a non-linear corresponding relation between compositional ratios of multi-component materials composed of a plurality of components and mechanical behaviors of the multi-component materials; input means for inputting an objective function and a constraint condition as optimization items by determining the objective function expressing the mechanical behaviors and determining the constraint condition which constrains an allowable range of at least one of the mechanical behaviors and the compositional ratios of the multi-component materials; and optimization calculation means for obtaining a compositional ratio of the multi-component materials which gives an optimal solution of the objective function based on the optimization items inputted from the input means by using the conversion system calculating means.

The non-linear corresponding relation between, on the one hand, the compositional ratios of the multi-component materials and a condition to be applied to the multi-component material and, on the one hand, the mechanical behaviors of the multi-component materials can be obtained by the conversion system calculation means.

The optimization calculation means can comprises: selecting means for selecting one compositional ratio of the compositional ratios of the multi-component materials included in the conversion system calculation means as a design variable; changing means for changing a value of the design variable selected from the conversion calculation means until the optimal solution of the objective function gives the optimal solution, while considering the constraint condition; optimal solution calculation means for calculating the value of the design variable until the optimal solution of the objective function is given by using the conversion system calculating means; and design means for designing a multi-component material based on the compositional ratio at the design variable which gives the optimal solution of the objective function.

The optimization calculating means is constructed as to effect the steps of: defining the compositional ratios of the multi-component materials in the conversion system determined in the conversion system calculation means as material base models to determine groups for selection composed of a plurality of material base models; for each of the material base models in the groups for selection, determining the objective function, the design variable, the constraint and an adaptive function which can be evaluated from the objective function; selecting two material base models from the groups; effecting at least one of producing new material base models by cross overing the design variables of the two material base models, at a predetermined probability with each other and producing new material base models by modifying in part the design variables at least one of the two material base models; obtain an objective function, a constraint condition and an adaptive function of the new material base models using the conversion system determined in the conversion calculation means by changing the design variables of new material base models; storing the material base models whose design variables have been changed and the material base models whose design variables have not been changed; repeating the storing steps until the number of the stored material base models reaches a predetermined number; determining whether or not new group comprising the stored material base models of the predetermined number satisfies a predetermined convergence condition; wherein if not, the new groups are defined as the groups for selection and the above steps are repeated until the new groups satisfy the predetermined convergence condition; and if the predetermined convergence condition is satisfied, designing a multi-component material based on the compositional ratio of the multi-component materials obtained from the design variable which gives the optimal solution of the objective function of one of the predetermined number of the stored material base models by using the conversion system determined in the conversion system calculation means while considering the constraint.

The conversion system calculation means comprises a multi-layered feed forward type neural network which has learned so as to convert the compositional ratios of the multi-component materials to the mechanical behaviors thereof.

The above mentioned design method of a multi-component material can provide a storage medium having a stored optimization analyzing program for a multi-component material. The storage medium includes a program according to the following procedures and is portable.

The storage medium having the stored optimization analyzing program for a multi-component material is a storage medium having a stored optimization analyzing program for design of a multi-component material by a computer. The optimization analyzing program is programmed to determine a non-linear corresponding relation between compositional ratios of multi-component materials and mechanical behaviors of the multi-component materials, to determine an objective function expressing the mechanical behaviors, and to determine a constrain constraining an allowable range of at least one of the mechanical behaviors and the compositional ratios of the multi-component materials and determine one of the compositional ratios of the multi-component material, which gives an optimal solution of the objective function, based on the corresponding relation, the objective function and the constraint to design the multi-component material based on the one of the compositional ratios.

The design of a multi-component material based on the compositional ratios of the multi-component materials conducts the steps of: selecting as a design variable one of the compositional ratios of the multi-component materials included in the determined corresponding relation based on the determined corresponding relation, the objective function, and the constraint; changing a value of the design variable selected from the determined corresponding relation until an optimal solution of the objective function is given while considering the constraint condition; and designing the multi-component material based on the compositional ratio of the multi-component materials obtained by the design variable which gives the optimal solution of the objective function.

The constraint condition can constrain an allowable range of at least one of the mechanical behaviors other than the determined objective function and the compositional ratios of the multi-component materials.

The change in the design variable which gives the optimal solution of the objective function is predicted while considering the constraint based on a sensitivity of the objective function which is a ratio of a changed quantity of the objective function to a unit change quantity of the design variable and a sensitivity of the constraint which is a ratio of a changed quantity of the constraint to a unit change quantity in the design variable, and a value of the objective function when the design variable is changed in a corresponding manner to a predicted quantity and a value of the constraint when the design variable is changed in a corresponding manner to the predicted quantity are calculated. Besides, a selected value of the design variable can be changed based on the predicted and calculated values while considering the constraint until the optimal solution of the objective function is given.

A design of a multi-component material based on the compositional ratios comprises the steps of defining the compositional ratios of the multi-component materials in the determined corresponding relation as material base models determine groups for selection composed of a plurality of material base models; for the material base models in the groups for selection, determining the objective function, the design variable, the constraint and an adaptive function which can be evaluated from the objective function; selecting two material base model from the groups, effecting at least one of producing new material base models by cross overing the design variables of the two material base models, at a predetermined probability with each other and producing new material base models by modifying in part the design variables of at least one of the two material base models; obtaining an objective function, a constrained condition and an adaptive function of the material base models whose design variables have been changed; storing the material base models whose the design variables have been changed and a material base models whose design variables have not been changed; repeating the storing steps until the number of the stored material base models reaches a predetermined number; deciding whether or not new groups comprising the predetermined number of the material base models stored satisfy a predetermined convergence condition; wherein if not, the above steps are repeating until the new groups satisfy the predetermined convergence condition; and if the predetermined convergence condition is satisfied, designing a multi-component material based on the compositional ratio of the multi-component materials obtained from the design variables which gives the optimal solution of the objective function in the predetermined number of the material base models stored by using the corresponding relation while considering the constraint.

As mentioned above, according to the present invention, the present invention has an effect that since a conversion system in which a non-linear correspondence between compositional ratios of multi-component materials composed of a plurality of components and mechanical behaviors of the multi-component material are correlated to each other is determined, the conversion system, in which a corresponding relation between compositional ratios of a plurality of compositions and mechanical behaviors thereof can be found out, can be obtained with high precision and lesser optionality.

The present invention has another effect that since one of a compositional ratios of multi-component materials which gives the optimal solution of an objective function by using the conversion system is obtained, the optimal design plan which is effective with a compositional ratio of multi-component materials can be achieved.

An optimal composition of a multi-component material, for example a quantity of carbon (% by weight), a rubber chemical (% by weight) and the like can directly be determined according to applied conditions such as production conditions, a cost and the like. As optimization items to be input, for example an abstract technical information such as a particle size or a particle ratio of carbon, can be used.

BRIEF DESCRIPTION OF THE DRAWINGS

FIGS. 13(a) and 13(b) are diagrams showing concave mapping functions of in which FIG. 13(a) is a diagram showing a concave mapping function of a curved type and FIG. 13(b) is a diagram showing a concave mapping function of a linear type.

BEST MODE OF THE INVENTION

Embodiments of the present invention will be described in referenced to the accompanying drawings in detail. An embodiment of the present invention is applied to an optimization apparatus in which an optimum rubber compound is sought. In an optimization apparatus of a first embodiment, an optimum composition of a multi-component material is obtained by an optimization calculation using as a conversion system a neural network obtained after being subjected to learning which is a non-linear prediction technique in which a neural circuit network of a higher animal is modeled in an engineering approach.

Figure 1:
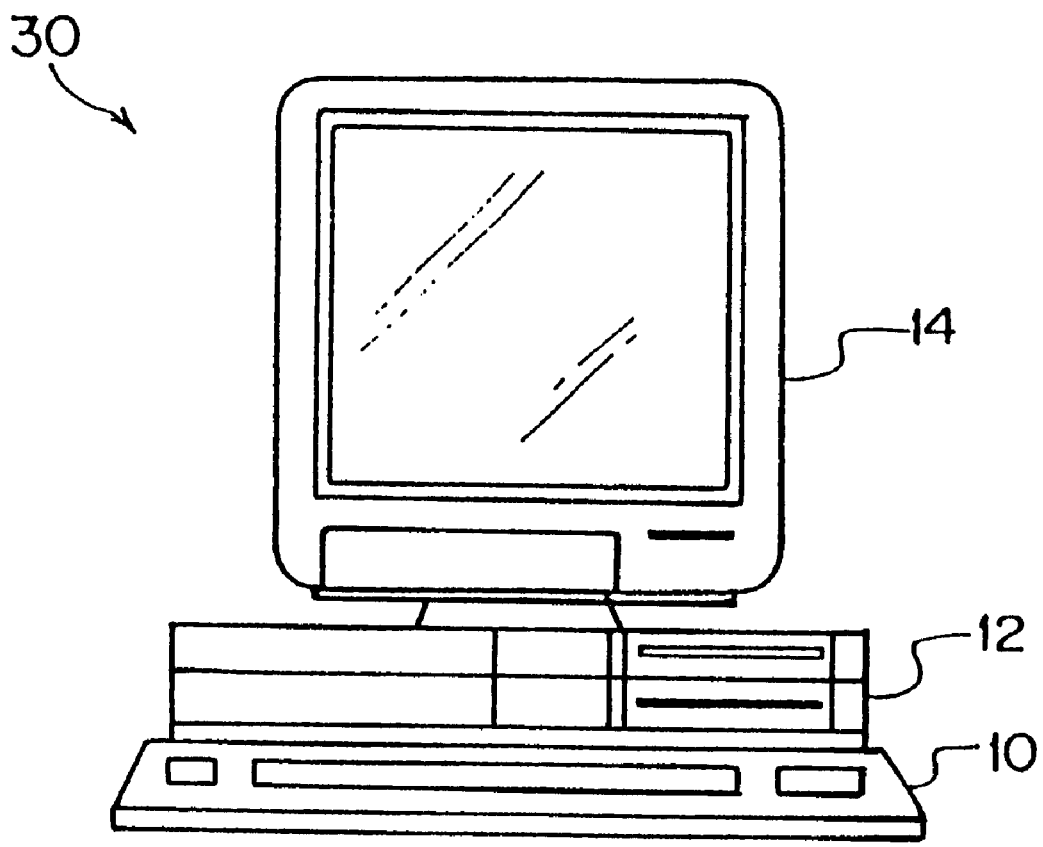
FIG. 1 is a view of an external appearance of an optimization apparatus according to one embodiment.

In FIG. 1, an optimization apparatus 30 which is used for executing an optimization of a material of the present invention is schematically shown. The optimization apparatus 30 comprises: a key board 10 for inputting data or the like; a computer main body 12 for predicting mechanical behaviors from compositional ratios of components of a multi-component material composed of a plurality of components and the like using a neural network by means of a non-linear prediction method according to a program stored in advance and calculating a design variable which makes constraint satisfied and optimizes (for example, maximize or minimize) an objective function; and a CRT 14 for displaying calculation results or the like obtained by the computer main body 12.

Figure 2:
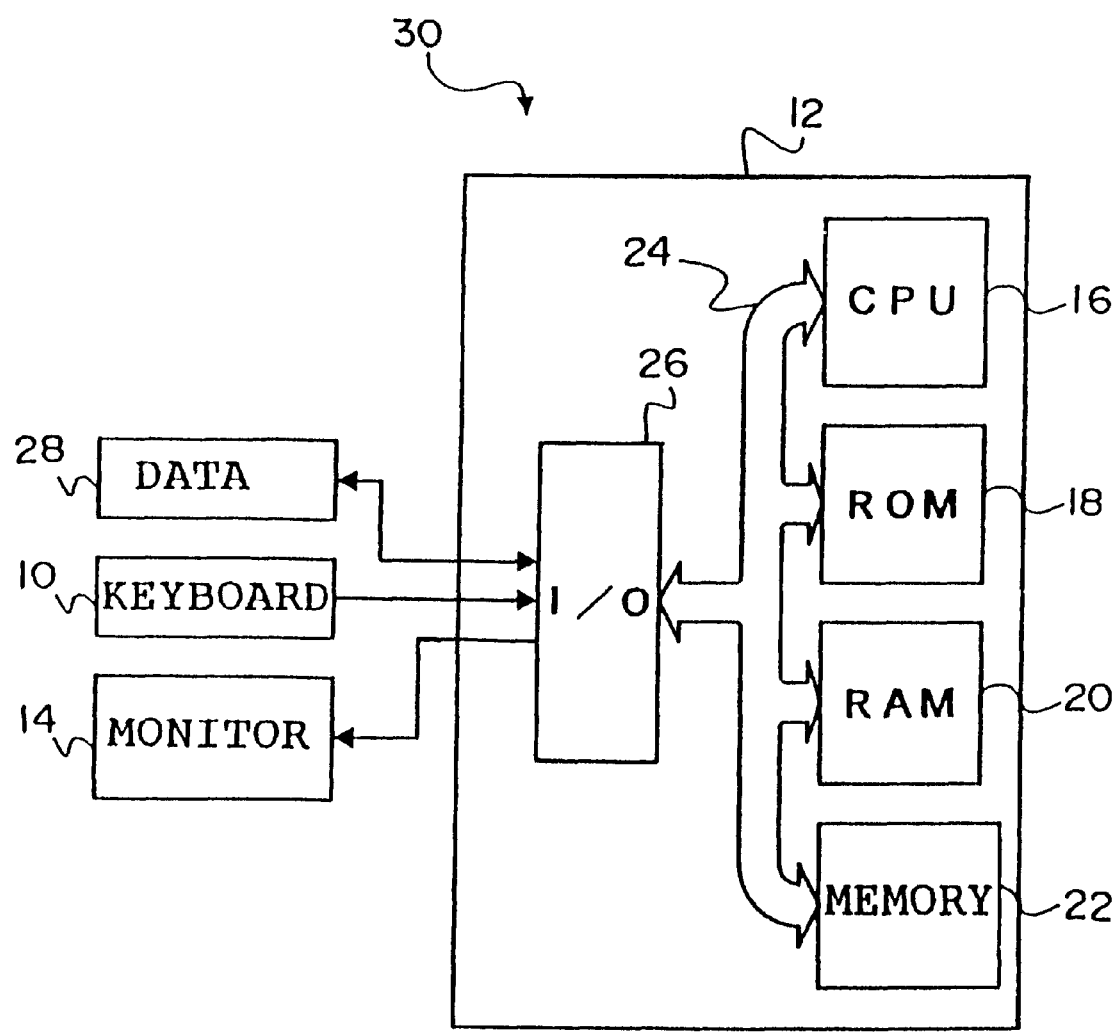
FIG. 2 is a block diagram schematically showing a structure of an optimization apparatus according to the embodiment.

As shown in FIG. 2 in a detailed manner, the optimization apparatus 30 comprises: the computer main body 12 including a microcomputer; a data input/output unit 28; a key board 10 through which data and commands are input; and a monitor 14. The computer main body 12 comprises: a CPU 16; a ROM 18; a RAM 20; a memory 22 storing a conversion system and the like (later detailed); an input/output device 26 (hereinafter referred to as I/O) to transmit data and the like between the other device and the main body 12; and a bus 24 connected so as to enable input/output of data or commands. A processing program later described is stored in the ROM 18. The data input/output device 28 is an unit for reading in from an exterior storage means when compositional ratios of multi-component materials, production conditions and mechanical behaviors(in the embodiment, a Young's modulus and the like) expressed in numeral values are stored in the exterior storage means but it is not necessary when the key board 10 is used as an input device.

Figure 3:
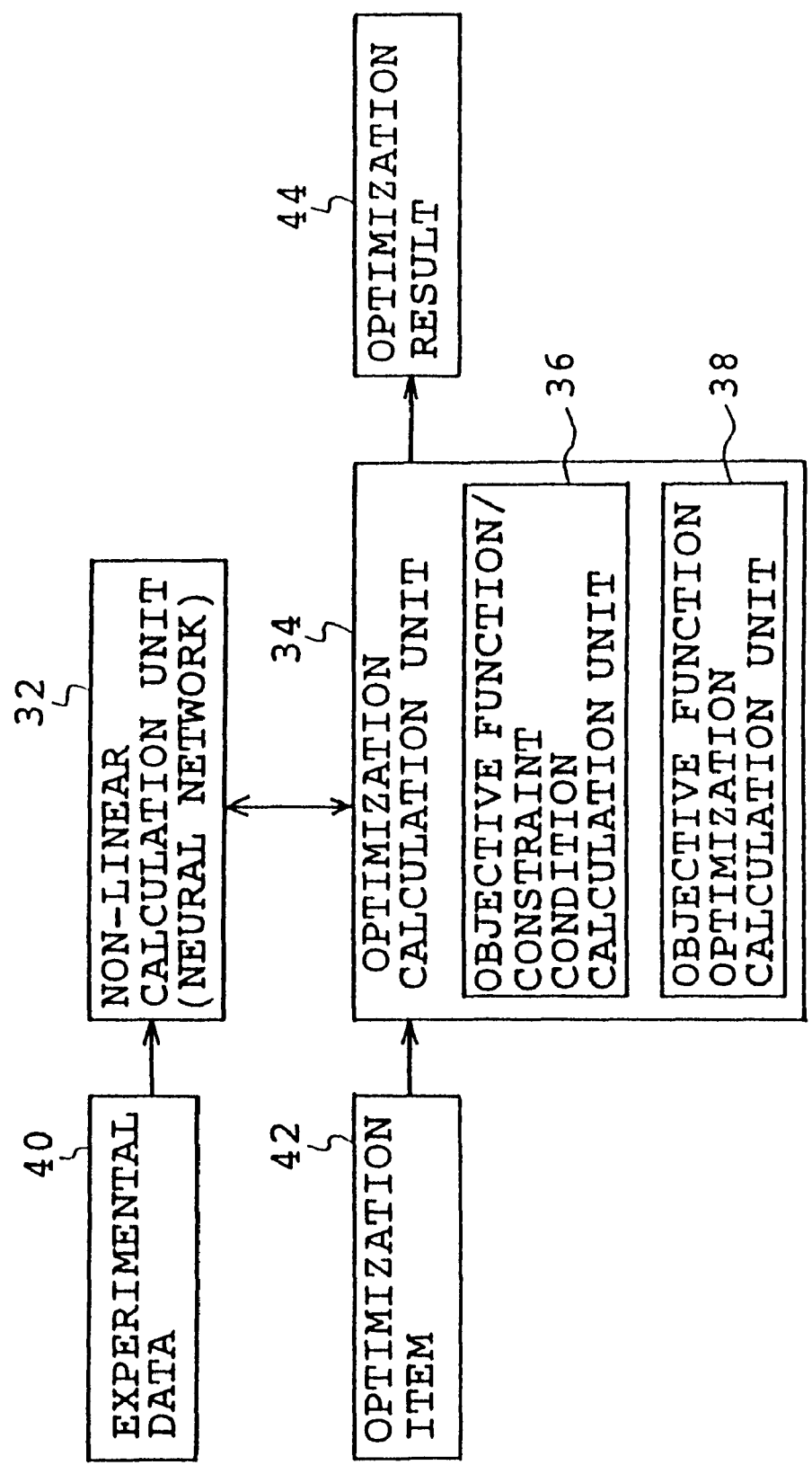
FIG. 3 is a block diagram showing functions of an optimization apparatus according to the embodiment.

FIG. 3 is a block diagram showing functions of the optimization apparatus 30. The optimization apparatus 30 of the embodiment outputs a compositional ratio of the multi-component materials corresponding to an optimized mechanical behavior while optimizing a mechanical behavior (which is called an objective function) while optimizing a mechanical behavior to be maximized or minimized.

The optimization apparatus 30 comprises in a functionally separated manner: a non-linear calculation unit 32, an optimization calculation unit 34, an experimental data input unit 40; an optimization item input unit 42; and an optimization result output unit 44. The non-linear calculation unit 32 functions as a calculation unit of the conversion system (later detailed) comprising a neural network and is constructed so as to obtain a conversion system in which compositional ratios of components and production conditions of a multi-component material, and mechanical behaviors of the multi-component material are mutually made to correlate with each other based on data input from the experimental data input unit 40. The conversion system here is a conversion system in which a conversion and inverse conversion thereof can be made in a one to one corresponding manner between the compositional ratios and production conditions of the multi-component materials and the mechanical behaviors thereof, and when the neural network which has been subjected to learning is expressed in a mathematical equation, the conversion system includes the mathematical equation and the coefficients. The experimental data input 40 is used to input data including compositional ratios, production conditions of multi-component materials, and mechanical behaviors corresponding thereto.

The optimization item input unit 42 inputs (1) a mechanical behavior (which is an objective function later described), such as a Young's modulus or tan δ to be maximized or to be minimized, (2) the mechanical behavior which provide constraint when it is maximized or minimized, a compositional ratio of multi-component materials and such, production conditions as a vulcanizing temperature, an environmental temperature or a humidity, (3) allowable ranges of the compositional ratio of the multi-component materials and the production condition, and (4) selection of an optimization related method, and parameters to be used when the method is employed. The optimization related methods are a mathematical programming, a genetic algorithm and the like but in the embodiment, an optimization approach according to a mathematical programming is selected.

The optimization calculation unit 34 optimizes an objective function until the objective function is converged and comprises an objective function/constraint calculation unit 36 and an objective function optimization calculation unit 38. The objective function/constraint condition calculation unit 36 predicts a mechanical behavior from a compositional ratio of multi-component materials composed of a plurality of components and a production condition by using the conversion system obtained by using the non-linear calculation unit 32 and the objective function optimization calculation unit 38 optimizes an objective function input through the optimization item input unit 42 until it is converged while satisfying a constraint.

The optimization result output unit 44 outputs a compositional ratio of multi-component materials and a production condition which has been optimized so as to satisfy an input optimization item(s) as a result of optimization which has been effected by the optimization calculation unit 34.

In the embodiment, the non-linear calculation unit 32 is constructed using a hardware resource shown in FIG. 2 and a software resource later described and it has not only a conversion function constructed by a conceptual neural network, as described later, but also a learning function which learns the conversion function. The non-linear calculation unit 32 can be a constitution which has only a conversion function without a learning function. That is, while the non-linear calculation unit 32, as described later, obtains the conversion system in which a correlation between, on the one hand, compositional ratios of multi-component materials and production conditions and, on the other hand, mechanical behaviors are established with each other, a conversion may be conducted between, on the one hand, the compositional ratios of the multi-component materials and the production conditions and the mechanical behaviors. Therefore, the corresponding relation between, on the one hand, compositional ratios of the multi-component materials and the production conditions, and, on the other hand, and the mechanical behaviors is learned in advance in another neural network, conversion coefficients of the another neural network obtained by learning are input and the conversion system in which the corresponding relation between the compositional ratios of the multi-component materials and the production conditions and on the other hand, the mechanical behaviors are established to each other using the conversion coefficient may be sought. That is, with any constitution in which conversion coefficients may be input, there maybe a function which exercises only a conversion between, on the one hand, the compositional ratios of the multi-component materials and the production conditions, and, on the other hand, the mechanical behaviors using the conversion coefficient. The correspondence is stored as a look-up table and the conversion may be conducted by reference to the stored look-up table.

The above mentioned non-linear calculation unit 32 has neurons of the number corresponding to the number of compositional ratios of a multi-component materials plus the number of production conditions as an input layer in order to make it possible to input respective values of compositional ratios of multi-component materials and respective values of production conditions and the unit has neurons of the number according to the number of mechanical behaviors as an output layer with an intermediate layer interposing therebetween. The neurons are connected by synapses to constitute a neural network. If the non-linear calculation unit 32 is input with the values of compositional ratios of multi-component materials and the values of production conditions after learning described later, the value of mechanical behaviors corresponding to the input are output. In a learning, known mechanical behaviors respectively corresponding to compositional ratios of multi-component materials and production conditions are input as a teacher and setting is conducted so that the mechanical behaviors respectively correspond to the compositional ratios of multi-component materials and the production conditions according to a magnitude of error differences between the output mechanical behaviors and the known mechanical behaviors.

Figure 4:
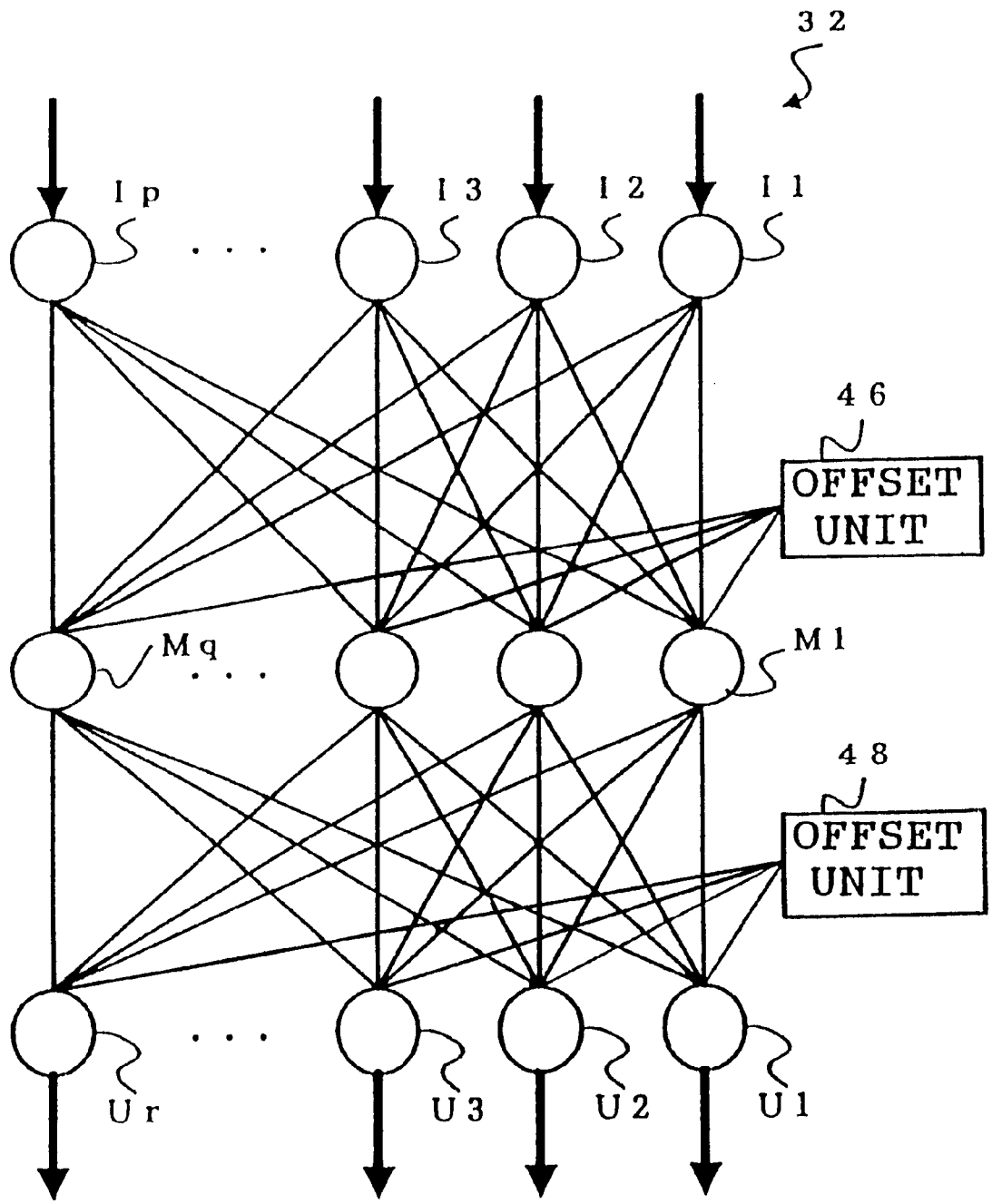
FIG. 4 is a diagram showing a conceptual structure of a neural network.

An example of a neural network used in the non-linear calculation unit 32, as shown in FIG. 4, comprises: an input layer comprising a predetermined number of units I1, I2, . . . , Ip (p>1) corresponding to the number of neurons; an intermediate layer comprising many units M1, M2 . . . , Mq (q>1); and an output layer comprising a predetermined number of output units U1, U2, . . . , Ur (r>1). The number of the units of the input layer and the number of the units of the output layer may be set in accordance to the numbers of component ratios of multi-component materials, of production conditions and of mechanical behaviors. Each unit of the intermediate layer is connected to an offset unit 46 for offsetting a value output from each unit of the intermediate layer by a predetermined amount, and each unit of the output layer is also connected to an offset unit 48 for offsetting a value from each unit of the output layer by a predetermined amount. In the units of the input layer, for example, quantities (% by weight) of carbon black, Si, a polymer and a rubber chemical, and particle diameters, and a particle diameter ratio of carbon black, and a cost can be used as input values. In the units of the output layer, a Young's modulus, a Poisson ratio, tan δ and a cost can be used as output values.

In the embodiment, each unit of the intermediate layer and output layer comprises a neural circuit element having sigmoid characteristics in which an input/output relation is expressed in a sigmoid function, and each a unit of the input layer comprises a neural circuit element having a linear input/output relation. Since each unit of the intermediate layer on and the output layer is constituted so as to have the sigmoid characteristics, each an output value can be a real number (a positive number).

Outputs from respective units of the intermediate and the output layers in the non-linear calculation unit 32 can be expressed by the following equations (1) and (2). When the number of synapses of the input side is p and a weight (joint coefficient of units) corresponding to a strength of a synapse joint is $w_{ij}$ ($1 \leq j \leq N$, $1 \leq i \leq p$) and an input signal is xj in a unit, a virtual internal state variable u corresponding to the average of membrane potentials of neurons can be expressed in the equation (1) and an output y can be expressed in the equation (2) by a non-linear function f expressing characteristics of a neuron.

$$u_j = \sum_{i=1}^{p} w_{ji} \cdot x_i + b_j \tag{1}$$

$$y_j = f(u_j) \tag{2}$$

wherein bj indicates an offset value supplied from an offset unit and $w_{ij}$ indicates a weight between the ith and jth units of respective different layers.

Therefore, if values of compositional ratios of multi-component materials and production conditions are respectively input into units of the input layer, outputs in accordance to the number of mechanical behaviors are respectively output from units of the output layer.

Characteristics of respective units of the input layer may be those that an input is output as it is. A weight of each unit (joint coefficient) of the non-linear calculation unit 32 (neural network) is corrected by learning so as to have an error in known experiment data minimized in learning processing, which is later described.

Figure 6:
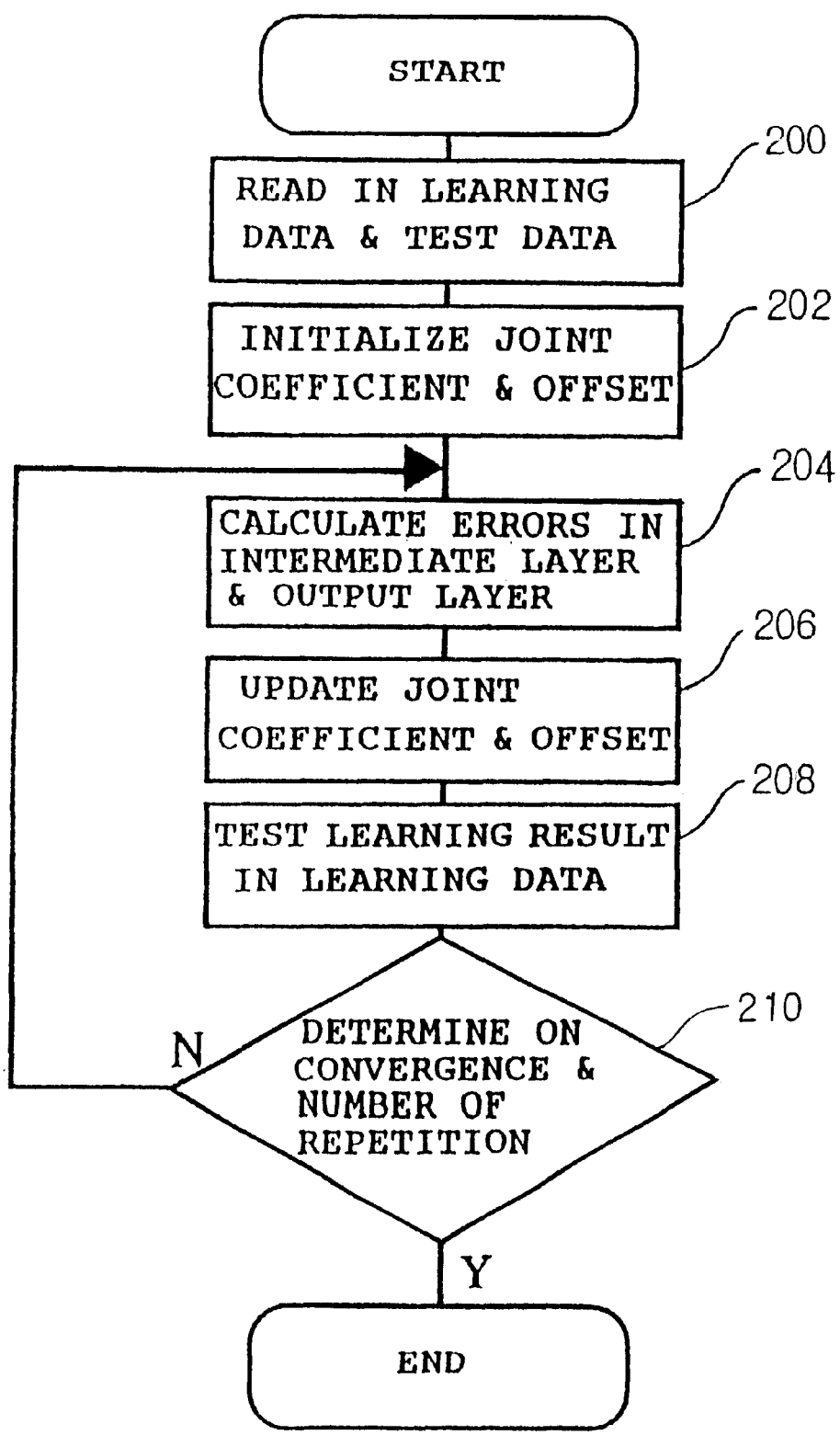
FIG. 6 is a flow chart showing a flow of a learning process of a neural network.

Learning processing of the neural network in the non-linear calculation unit 32 will in detail be described in reference to FIG. 6. In the embodiment, rubber member is formed on the basis of each value of the compositional ratios of multi-component materials and each value of the production conditions but also values indicating mechanical behaviors of rubber member thus formed are in advance measured. Rubber members having different compositional ratios and/or different production conditions are formed and measured and thereby experimental data of respective correspondences between, on the one hand, the compositional ratios of the multi-component materials and the production conditions, and on the other hand the mechanical behaviors are obtained, which are used as a plurality of teacher data in learning. A predetermined number of the plural teacher data (for example, 90%) is used for learning data and the other (for example, 10% as the residual) are used as test data. The reason why the experimental data is divided to the above two group is that one group of the experimental data are used as data which are used for learning in the neural network and the other group is used as data with which it is confirmed whether or not the neural network has learned optimally. Each value of compositional ratios and production conditions is used as input teacher data and each value of mechanical behaviors of rubber members is used as output teacher data.

In Step 200, learning data and test data which have been obtained are read out. In Step 202, initialization is effected by setting in advance joint coefficients (weights) of respective units in the neural network and setting offset values to respective predetermined values. In Step 204, errors in respective units of the intermediate and output layers are obtained in order to cause the neural network to learn with use of a plurality of learning data in which compositional ratios and production conditions are known.

Errors in the output layer can be differences between the leaning data and the mechanical behaviors. If at least one of respective joint coefficients and respective offset values are gradually changed errors in the output layer, that is, errors in the units can be minimized. Errors in the intermediate layer can inversely be obtained by a calculation such as an inverse error propagation method with use of the errors in the output layer.

In Step 206, the joint coefficients and the offset values which have been already obtained are updated (rewritten) and in Step 208, test data are respectively tested by the updated joint coefficients and offset values in the neural network so that data expressing mechanical behaviors of the rubber member are obtained as test results. In Step 210, it is determined whether or not the values of the test result has been converged according to an judgment about whether or not the values of the test result which have been obtained in the Step 208 are in a predetermined range as a decision reference of convergence or whether or not the number of repetitions of the above steps has reached a predetermined number. If yes, the routine is terminated. On the other hand, if not, process is returned back to the Step 204 and the above mentioned processing is repeated. Accordingly, when the learning data are input, respective joint coefficients and offset values are determined in such a manner that the errors in respective units of the intermediate and output layers may be minimized.

In such a manner, the neural network is made to learn by using a plurality of experimental data in which the compositional ratios and the production conditions are known. That is, learning is conducted such that the errors between the output values from the output layer of the neural network and the teacher signals are minimized. If the learning is conducted, the values of the mechanical behaviors of a rubber member are output in the non-linear calculation unit 32 when the compositional ratios and the production conditions are input.

After the above processing is finished and a sufficient learning of the neural network is conducted, a structure of the neural network, that is the joint coefficients and the offset values, are stored in a memory 18 and a conversion system may be constructed.

In the above, the case where the neural network is used as the non-linear calculation unit 32 has been described, the conversion system utilizing a response surface methodology in a polynominal as shown in the following equation (3), can also be employed.

$$y = a_0 + \sum_{i=1}^{p} a_i x_i + \sum_{i=1}^{p}\sum_{j=1}^{p} b_{ij} x_i x_j \quad (3)$$

Figure 5:
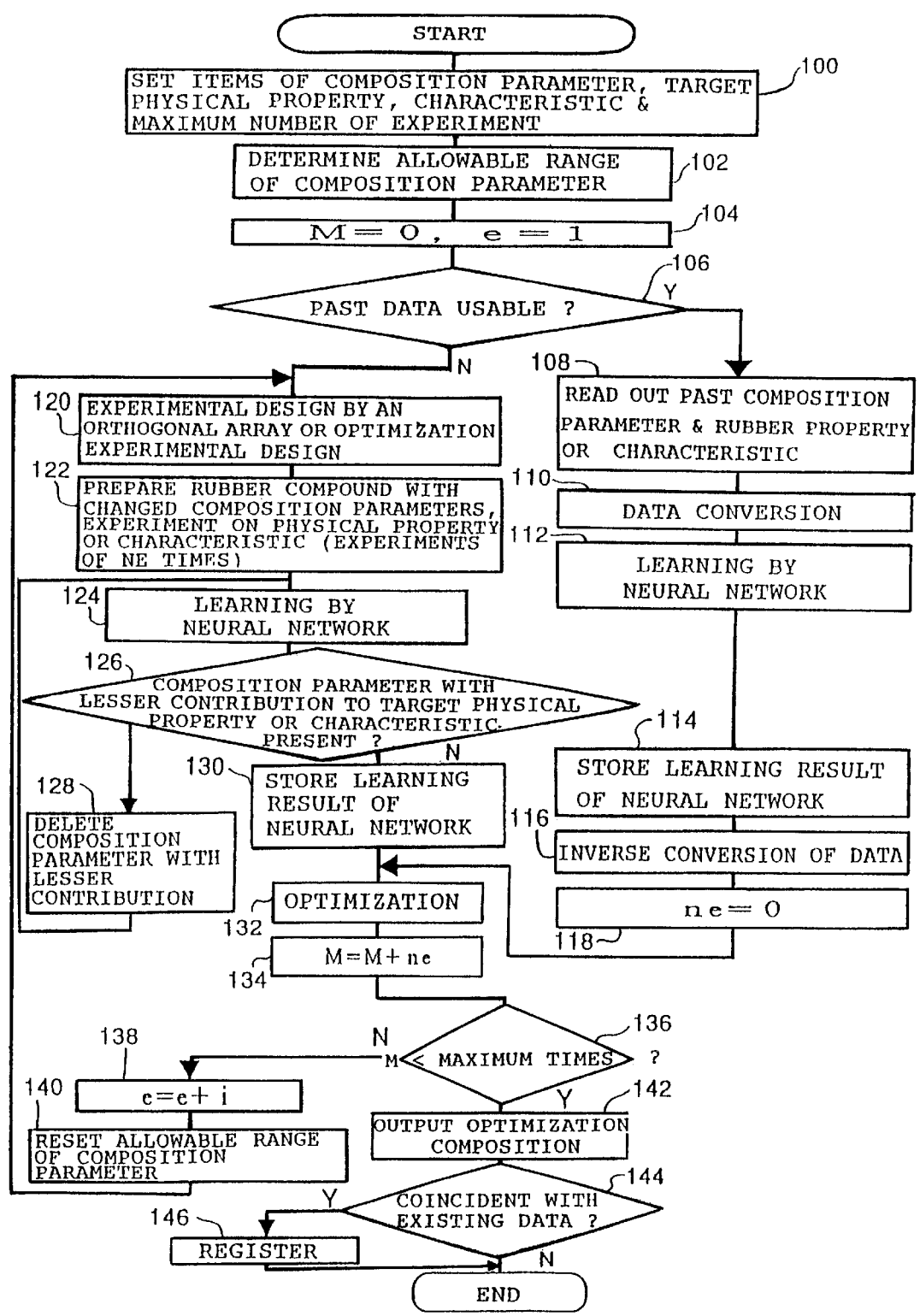
FIG. 5 is a flow chart showing a flow of operation of an optimization apparatus according to the embodiment.

Then, operation of the optimization apparatus 30 of an embodiment of the present invention will further be described in reference to a flowchart of FIG. 5. When an electric source of the optimization apparatus 30 is turned on or an instruction of execution start is input in the optimization apparatus 30 from a key board, processing is advanced to Step 100 of FIG. 5, in which composition parameters $x_i$ (i=1 to p), representing quantities or a compositional ratios of components of multi-component materials and a cost, and target physical properties, characteristics (mechanical behaviors) such as a Young's modulus and the like, and the maximum number of experiments are set in the optimization apparatus 30. That is, it is set about which target physical property, or characteristic is need to be improved by changing a quantities or the ratio of the components and the cost (the composition parameter). In this case, it is set about what accumulated number of experiments an optimal composition parameter are desired to be determined in.

In Step 102, an allowable range of the composition parameter $x_i$ which has been set in the Step 100 is set, wherein $x_i^L \leq x_i \leq xi^U$ ($x_i^L$ is a lower limit value and $xi^U$ is an upper limit value) and then in Step 104, the number M of experiments and a variable e indicating a position of a composition parameter are initialized (M=0, e=1).

In Step 106, it is determined whether or not experimental data in the past can be used for the composition parameter $x_i$, and the target physical properties, characteristics which has been set in Step 100. If the decision Step 106 is yes, the process proceeds to Step 108. However, if not the parameter and the like have to be newly obtained, the process proceeds to Step 120.

In the Step 120, the composition parameter is determined by determining which composition parameter $x_i$ is changed to conduct an experiment with use of an orthogonal array, an optimal experimental design or the like. The determination of the composition parameter is conducted by use of a method described in "Box and Draper; Empirical Model Building and Response Surfaces", John Wiley & Sons, New York.

In Step 122, a multi-component material is formed by blending rubber materials on the basis of the quantities or the ratio of components of multi-component materials in accordance to the experimental design determined in the Step 120 and an experiment for measuring physical properties, characteristics of the multi-component material thus formed is effected to obtain experimental data. The number of times of total experiment is indicated by $n_e$.

In Step 124, as described above, learning is conducted for the neural network. That is, the learning is carried out for the neural network in such a manner that respective values of composition parameters are used as the values input to the input layer and respective values of physical properties, characteristics of a rubber are used as the values output from the output layer.

In subsequent Step 126, a determined is made about whether or not there is any composition parameter which contributes to the target physical property, characteristic at a lesser extent. For example, by calculating a sensitivity which shows a tendency of change in the rubber physical property, characteristic in the output layer for a small change in a composition parameter $x_i$ input to at least one unit of the input layer and a degree of reduction in prediction precision of a rubber physical property, characteristic of the output layer when an output from at least one unit of the input layer is set at zero, and the composition parameter which has a lesser contribution is determined. The reason is that the composition parameter, which has a small sensitivity, and whose input can be neglected without a reduction in prediction precision, is considered to have a lesser contribution.

When there is a composition parameter which has a lesser contribution, the decision of the Step 126 is made affirmative. In Step 128, the composition parameter with a lesser contribution $x_i$ is deleted and a second learning is conducted by the other composition parameters after the deletion (Step 124). On the other hand, when no composition parameter with a lesser contribution is present, the decision of Step 126 is made negative and a correlation between the input layer (composition parameters) of the neural network which has been subjected to learning and the output layer (rubber physical properties, characteristics) is stored in Step 130. That is, a joint coefficient and an offset value are stored.

Figure 7:
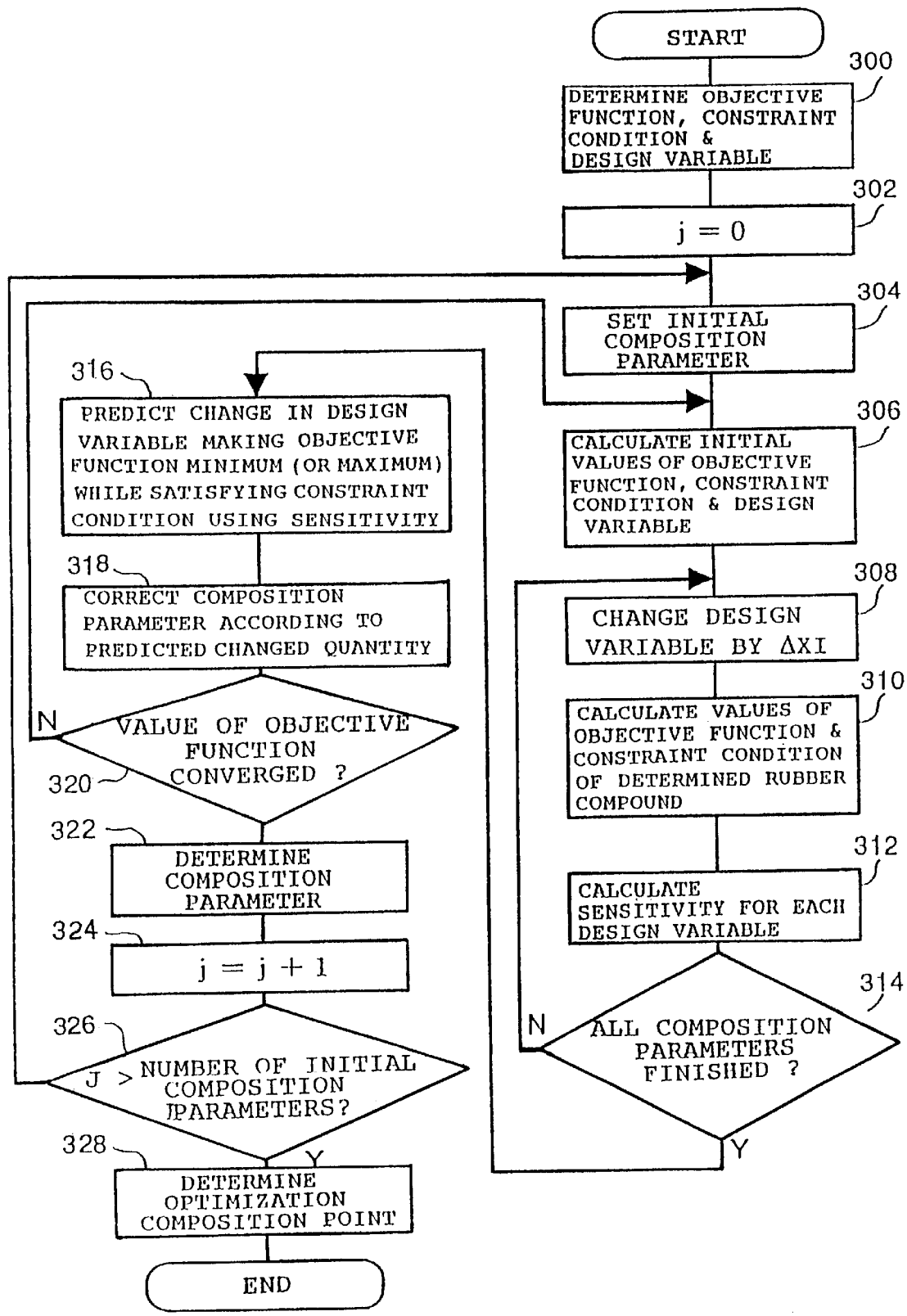
FIG. 7 is a flow chart showing a flow of an optimization process of an optimization apparatus according to a first embodiment.
Figure 8:
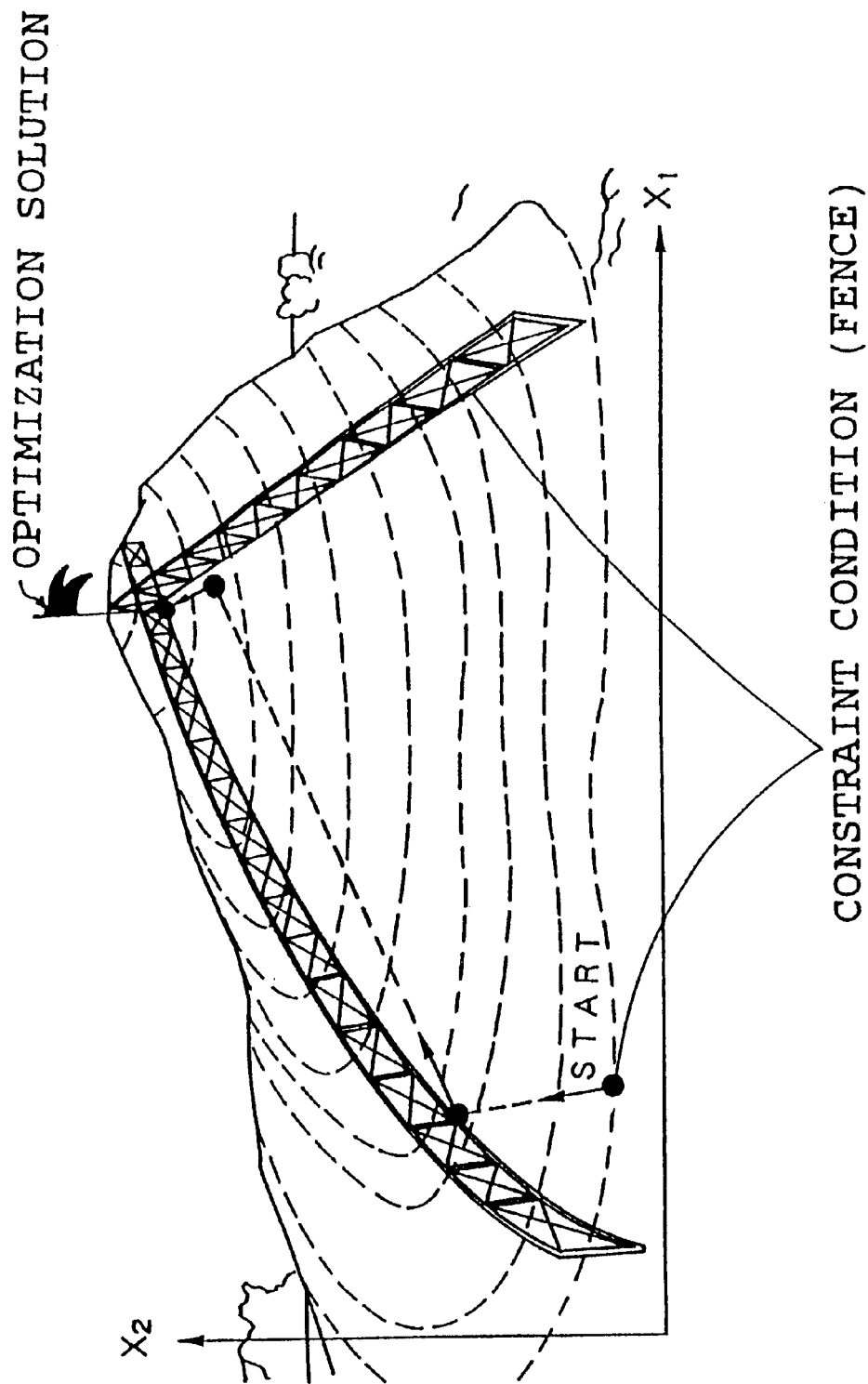
FIG. 8 is a conceptual view showing an image for illustrating an optimization of the present invention.
Figure 9:
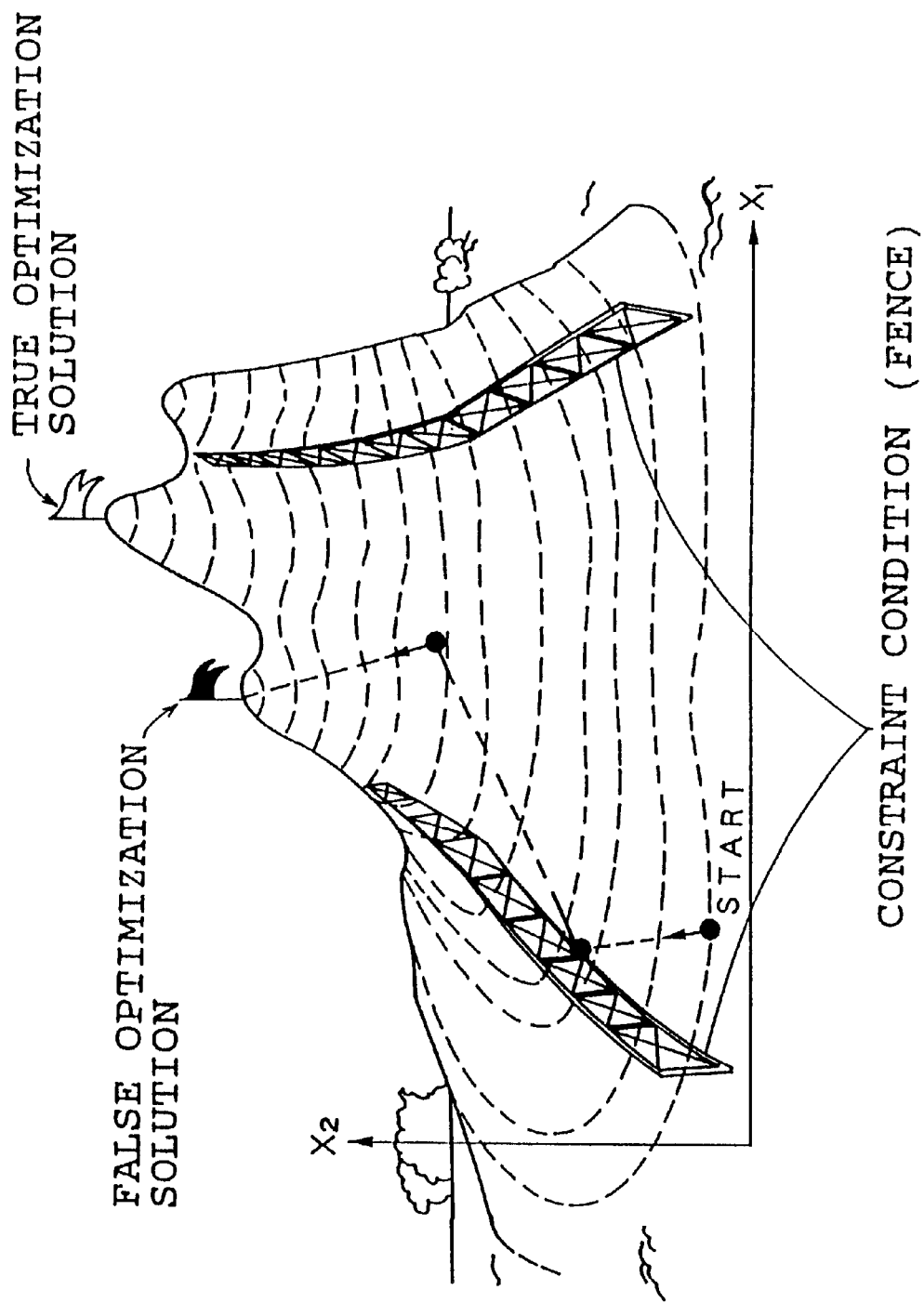
FIG. 9 is a conceptual view showing another image for illustrating an optimization of the present invention.

In subsequent Step 132, the best composition parameter $x_i$ is obtain by optimization of an objective function in such a manner to be described later using the correlation between the stored input layer (composition parameters) and stored output layer (rubber physical properties, characteristics) (see FIG. 7).

When the optimization is completed, the number M of the times of experiment is increased so as to be M=M+$n_e$ in Step 134. It is determined whether or not M<(the maximum set number of experiments) in Step 136 and the process proceeds to Step 138 when an M is smaller than the maximum set number.

In Step 138, a variable, e, is incremented and the allowable ranges of composition parameters are reset as shown in the following equations (4) to (6) in Step 140, followed by returning to the Step 120. If such processing is repeated, the precision of an optimum composition parameter $x_i^{OPT}$ can be improved. Resetting of the allowable ranges in the Step 140 is conducted by setting narrower ranges than those of the composition parameters determined in the Step 102 and designing second experiment is conducted in the narrowed ranges in the Step 120.

$$x_i^{Lnew} \leq x_i \leq x_i^{Unew} \quad (4)$$

$$x_i^{Lnew} = \text{Min}\left(x_i^L, x_i^{OPT} - \frac{x_i^U - x_i^L}{NN}\right) \quad (5)$$

$$x_i^{Unew} = \text{Max}\left(x_i^U, x_i^{OPT} - \frac{x_i^U - x_i^L}{NN}\right) \quad (6)$$

wherein NN is a coefficient to determine a degree of narrowing of an allowable range of a composition parameter and it is preferable that an NN is roughly set in the range of 1.5 to 5.

On the other hand, when a negative judgment is obtained in the Step 136, that is, when the number of experiments is larger than the predetermined maximum number of times of experiment, a composition parameter obtained in Step 142 as the latest is output as the optimum composition. In Step 144, it is determined whether or a similar composition is present in the past data and in the case of a negative judgment, in Step 146 a physical property or characteristic of a rubber with the optimum composition is made to enter into a data base for registration, such as an external storage apparatus or the like by way of a memory 22 or a data input/output unit 28. At this point, a second group of experiments may be executed in order to obtain a physical property or characteristic.

The maximum number of times of experiment is a constant which is determined in consideration of a cost required for experiments, a time required for obtaining the optimum composition and the like.

When a positive judgment is made in the Step 106, in Step 108 composition parameters, rubber properties or characteristics in the past associated with items set in the Step 100 are read out from a previously prepared data base and in Step 110, read-out data $C_i$ (i=1 to p) are converted so as to have a smaller kurtosis and skewness using the following equation (7) to (10).

$$\text{Kurtosis} = \frac{1}{p}\sum_{i=1}^{p}\left(\frac{c_i - \mu}{\sigma}\right)^4 - 3 \quad (7)$$

$$\text{Skewness} = \frac{1}{p}\sum_{i=1}^{p}\left(\frac{c_i - \mu}{\sigma}\right)^3 \quad (8)$$

$$\mu = \frac{1}{p}\sum_{i=1}^{p}c_i \quad (9)$$

$$\sigma = \frac{1}{p}\sum_{i=1}^{p}(c_i - \mu)^2 \quad (10)$$

In Step 112, learning of the neural network is effected in the same manner as in Step 124 and in Step 114, a result of the learning is stored as in the Step 130. In the subsequent Step 116, an inverse conversion which is inverse to the conversion in the Step 110 is conducted in order to return to the experimental data. In Step 118, a total number of experiments, $n_e$, is reset (=0) and the process proceeds to Step 132.

An optimization processing will in detail be described in Step 132 shown in FIG. 5. In Step 300 of FIG. 7, there are determined an objective function which represents physical properties, characteristics of a rubber to be improved, a constraint condition that constrains physical properties, characteristics of the rubber which are not allowed to be deteriorated in the improvement and a design variable which determines composition parameters related to a rubber compound and in Step 302, a variable, j, indicating the number of the composition parameters is reset (=0).

In Step 304, a composition parameter which is used as an initial value in optimization is set. In optimization of composition of multi-component materials, a solution space for optimal solution is required to be obtained by conducting optimization starting from a different initial value, since a shape expressing compositions of the multi-component materials has a multi-peak configuration if an input value is grasped in a three dimensional image by plotting input values (for example quantities of carbon black and rubber chemicals) on a plane, which is two dimensional, and further plotting an objective function along a height direction. As an initial value, for example, the following equation (11) can be employed.

$$x_i^{start} = x_i^L + \frac{x_i^U - x_i^L}{Munit} \cdot k \quad (11)$$

where $x_i$ (i=1 to p) is a composition parameter, $x_i^L \leq x_i \leq x_i^U$ is a range in which a composition parameter can assume a value, k=0 to Munit and Munit is the number of divisions of an allowable range of a compositional parameter.

In Step 306, output by the neural network is executed with use of the initial composition parameter, which is set in the Step 304, as an input and physical property, characteristic corresponding to the input composition parameter of a rubber is predicted. An objective function and a constraint condition are calculated using the result of the prediction.

In subsequent Step 308, a composition parameter $x_i$ which has been set in the Step 304 is changed by $\Delta x_i$ at each time in order to change the composition parameter and in Step 310, a value of the objective function $OBJ_i$ and a value of a constraint condition $G_i$ after a design variable is changed by $\Delta x_i$ are calculated and in Step 312, a sensitivity $dOBJ/dx_i$ of the objective function which is a ratio of a changed quantity to a unit changed quantity of a design variable and a sensitivity $dG/dx_i$ of a constraint condition which is a ratio of a changed quantity to a unit changed quantity of a design variable are calculated for each design variable according to the following equations (12) and (13).

$$\frac{dOBJ}{dx_i} = \frac{OBJ_i - OBJ_o}{\Delta x_i} \qquad (12)$$
$$= \frac{OBJ(x_i + \Delta x_i) - OBJ(x_i)}{(x_i + \Delta x_i) - (x_i)}$$

$$\frac{dG}{dx_i} = \frac{G_i - G_o}{\Delta x_i} \qquad (13)$$

With the sensitivities, it can be predicted how much a value of the objective function is changed when the design variable is changed by $\Delta x_i$. The prediction process, that is, an optimization process of a composition of multi-component materials is analogous to mountain climbing and prediction of a change in a value of the objective function corresponds to designate a direction of climbing a mountain.

In Step 314, it is determined whether or not calculation on all composition parameters are completed and if the calculation is not completed, the Steps 308 to 312 are repeatedly executed.

In Step 316, a change in the design variable which minimizes (or maximizes) the objective function while the constraint condition is being satisfied is predicted by means of a mathematical programming with use of sensitivities of the objective function and the constrained condition. With use of the predicted value of the design variable, in Step 318, not only is each composition parameter corrected, but also values of the objective function are calculated based on the corrected composition parameters. In Step 320, a difference between a value of the objective function OBJ calculated in the Step 318 and the initial value $OBJ_0$ of the objective function calculated in the Step 306 is compared with a threshold value input in advance and thereby it is determined whether or not the value of the objective function is converged. In the Step, thereafter, if the value of the objective function is not converged, the Steps 306 to 320 are repeatedly executed using an obtained value of the design variable in the Step 316 as an initial value, but if it is judged that a value of the objective function has been converged, a value of the design variable at this point is regarded a value of the design variable which makes the objective function the best while the constraint condition is being satisfied, a composition parameter is determined using the value of the design variable in Step 322 and in Step 324, a variable, j, is incremented so that the process proceeds to Step 326.

In the Step 326, it is determined whether or not vaariable, j, exceeds an allowable number of initial composition parameters: $(1+Munit)^p$ and if not, the process is made to return to the Step 304 and the Steps 304 to 326 are repeatedly executed while values of the initial composition parameters are modified.

On the other hand, when a positive judgment is made in the Step 326, the optimum composition is determined in Step 328 and the routine is thus terminated. The determination of the optimum composition in Step 328 is to obtain it in consideration of the following two conditions, wherein the optimum composition is determined so as to have a larger degree of coincidence with a condition.

The conditions are that:

(1) the objective function OBJ has a small value, wherein physical properties, characteristics selected as an objective function, which is smaller, is set and if a larger one is better, the larger value is set with a negative sign attached before the same larger value and (2) even if a composition parameter is changed a little in the vicinity of an obtained optimal solution, neither the objective function nor the constraint condition is changed so much.

In the embodiment, as mentioned above, since learning of a corresponding relation between, on the one hand, compositional ratios of a plurality of components and production conditions and, on the other hand, mechanical behaviors of a material by the neural network has been conducted by use of experimental data in the non-linear calculation unit in order to determine the conversion system, there is no need for assuming a functional form as means for calculating the conversion system and the conversion system, in which a corresponding relation between, on the other hand, compositional ratios of a plurality of components and production conditions and, on the other hand, mechanical behaviors of a material is found, can be formed with a high precision and a lesser optionality. If the conversion system and the optimum calculation unit are combined a scheme of an optimal design of a material which is useful can be output.

The second embodiment will be described. The embodiment is to effect optimization by means of a genetic algorithm instead of a sensitivity analysis (FIG. 7) in the above embodiment. Since the second embodiment has almost the same structure as that of the above mentioned embodiment, the same members as those of the above mentioned embodiment is indicated by the same reference numerals as those of the above mentioned embodiment and detailed descriptions on the same members are omitted.

Figure 10:
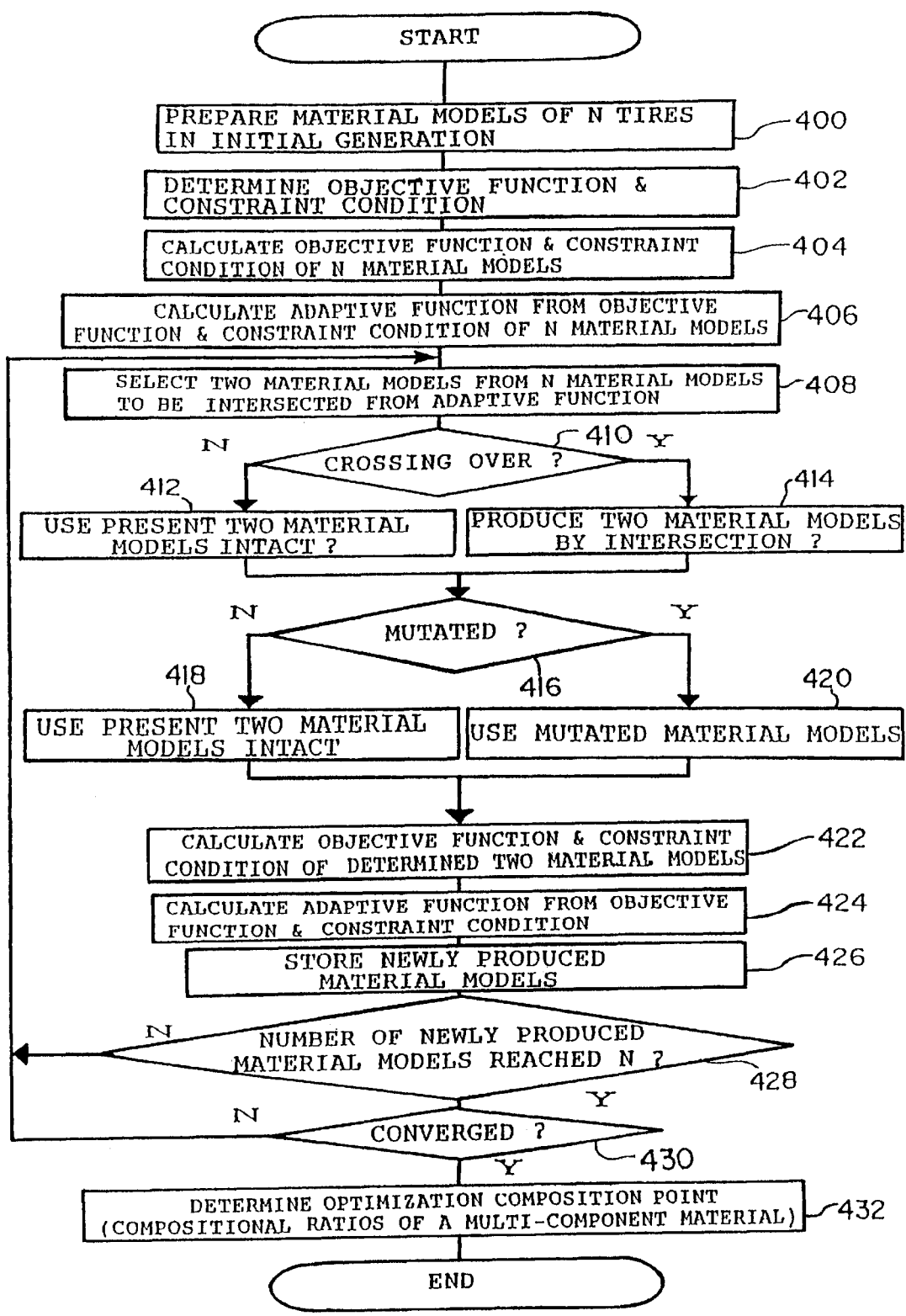
FIG. 10 is a flow chart showing a flow of an optimization process of a second embodiment.

FIG. 10 shows a processing routine of an optimization processing program of the second embodiment. After the Step 132 in FIG. 5 is executed, a processing routine shown in FIG. 10 is executed and in Step 400, modeling of N tires is effected. Each corresponding relation between composition parameters $r_{ij}$ (i=1 to p, j=1 to N) indicating quantities or ratios of components of multi-components and a cost, and a target physical property, characteristic, such as a Young's modulus, is modeled as a material model. Modelings of N times are to produce N inputs I1 to Ip based on a table of random numbers which is to be input to the input layer of the neural network shown in FIG. 4, wherein N is in advance input by an operator.

In Step 402, an objective function and a constraint condition are determined. That is, there are determined an objecting function representing physical properties, characteristics to be improved or newly desired and a constraint condition which constrains deterioration of a physical property, characteristic which is not allowed to be deteriorated in company with the improvement (determination of an objective function OBJ and a constraint condition G). In Step 404, objective functions $OBJ_J$ and constraint conditions $G_J$ for respective design variables $r_{iJ}$ of N material models are calculated.

In Step 406, adaptive functions $F_J$ of respective N models are calculated according to the following equation (14) using respective objective functions $OBJ_J$ and constraint conditions $G_J$ obtained in the Step 404. In the embodiment, a value of the adaptive function (degree of adaptability) becomes larger as a value of an objective function $OBJ_J$ becomes larger and a value of a constraint condition $G_J$ becomes smaller, for example, in order to optimize a Young's modulus, a Poisson ratio, tan δ and a cost.

$$\Phi_J = -OBJ_J + \gamma \cdot \max(G_J, O)$$
$$F_J = -\Phi_J \qquad (14)$$

$$F_J = 1/\Phi_J \text{ or } F_J = -a \cdot \Phi_J + b$$

$$a = \frac{\Phi_{avg}(c-1)}{(\Phi_{avg} - \Phi_{min})}$$

$$b = \frac{\Phi_{avg}(c - \Phi_{min})}{(\Phi_{avg} - \Phi_{min})}$$

$$\Phi_{avg} = \frac{\sum_{J=1}^{N} \Phi_J}{N}$$

wherein c is a constant, γ is a penalty factor, $\Phi_{min}=\min(\Phi_1, \Phi_2, \ldots, \Phi_N)$, and $\Phi_J$ is a penalty factor of the Jth material model among the N material models, wherein J=1, 2, 3, ... N and c and γ are input by an operator in advance.

In Step 408, two models which cross over with each other are selected from N material models. As a selecting method, a generally known adaptability proportional strategy is used and a probability $P_L$ in selection of an individual 1 among N material models is expressed by the following equation.

$$P_L = \frac{F_L}{\sum_{J=1}^{N} F_J}$$

wherein $F_L$ is an adaptive function of an individual 1 among the N material models and $F_J$ is an adaptive function of the Jth material model of the N material models, where J=1, 2, 3, ... N.

In the embodiment, while the adaptability proportional strategy is used as the selecting method, there may be used an alternative, such as an expected value strategy, a rank strategy, an elite conserving strategy, a tournament selection strategy or a GENITOR algorithm or the like, as shown in a book titled "Genetic Algorithm" compiled by Hiroaki Kitano.

In Step 410, it is determined whether or not two selected material models are caused to cross over each other at a probability T which the operator has input in advance. The intersection mentioned herein means that the two selected material models partially exchange for each other in elements constituting themselves, as later described. In a negative decision, that is, if the two models are not caused to cross over each other, the two models are kept intact in Step 412 and the process proceeds to Step 416. On the other hand, if the two models are caused to cross over each other in a positive decision, the two models are caused to cross over each other in Step 414, as described later.

Figure 11:
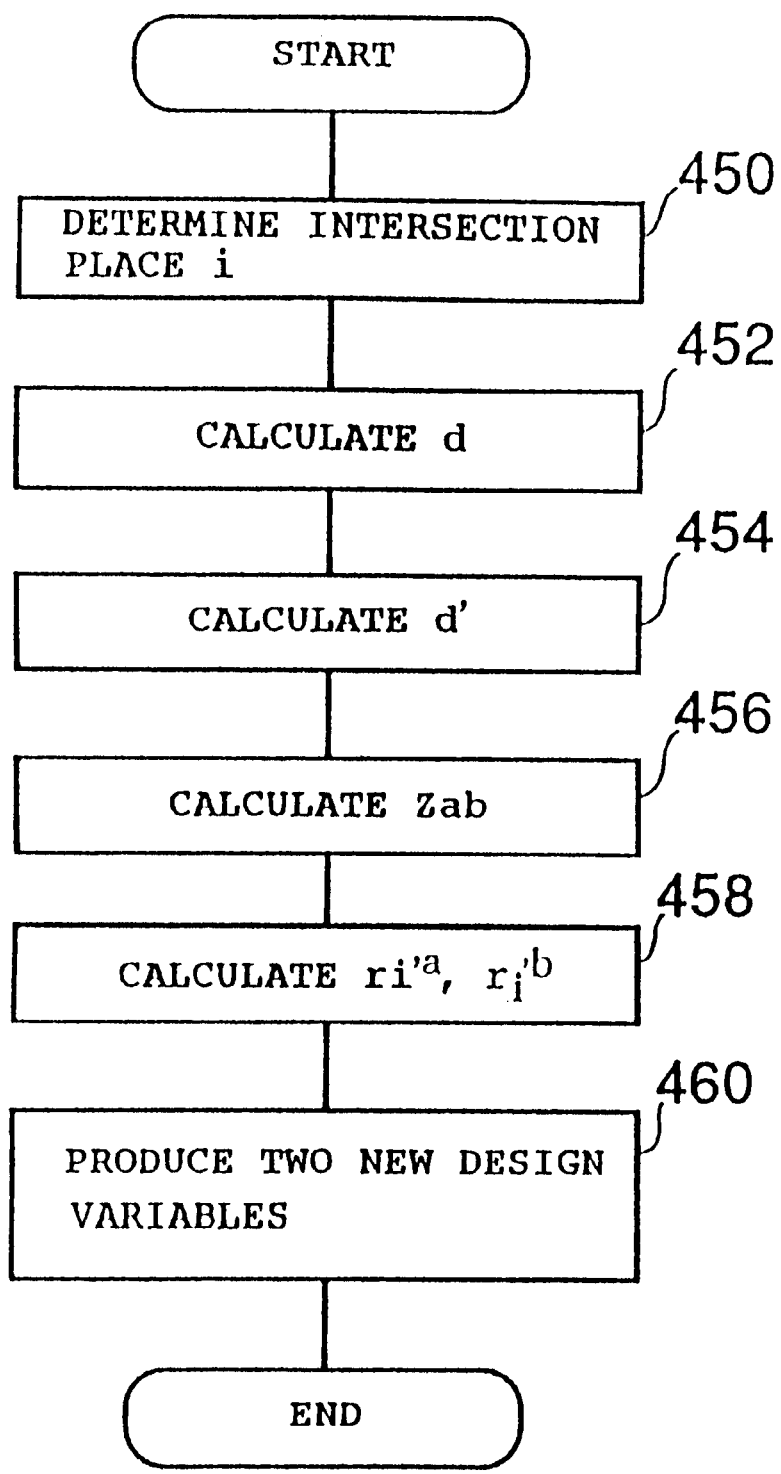
FIG. 11 is a flowchart showing a flow of an intersecting process.

Intersection of the two material models is performed by an cross overing routine shown in FIG. 11. In the Step 408 of FIG. 10, the two selected material models are respectively named as model "a" and model "b", and the design variables of the material models "a" and "b" are expressed by design variable vectors including a list, wherein a design variable vectors $Vr^a$ of the material model "a" is $Vr^a=(r_1^a, r_2^a, \ldots r_{n-1}^a)$ and a design variable vectors $Vr^b$ of the material model "b" is $Vr^b=(r_1^b, r_2^b, \ldots r_i^b \ldots r_{n-1}^b)$. In Step 450 of FIG. 11, with random numbers produced in advance, an cross overing place i regarding the design variable vectors of the material models "a" and "b" are determined according to the random numbers.

In Step 452, with design variables $r_i^a$ and $r_i^b$ of the material models "a", "b" which have been determined to be subjected to cross overing, a distance, d, is obtained by the following expression.

$$d=|r_1^a - r_1^b|$$

In Step 454, a normalized distance d' is obtained by the following expression using the minimum value $B_L$ and the maximum value $B_u$ in the ranges where $r_i^a$ and $r_i^b$ can be set.

$$d' = \frac{d}{B_u - B_L}$$

Figure 12A:
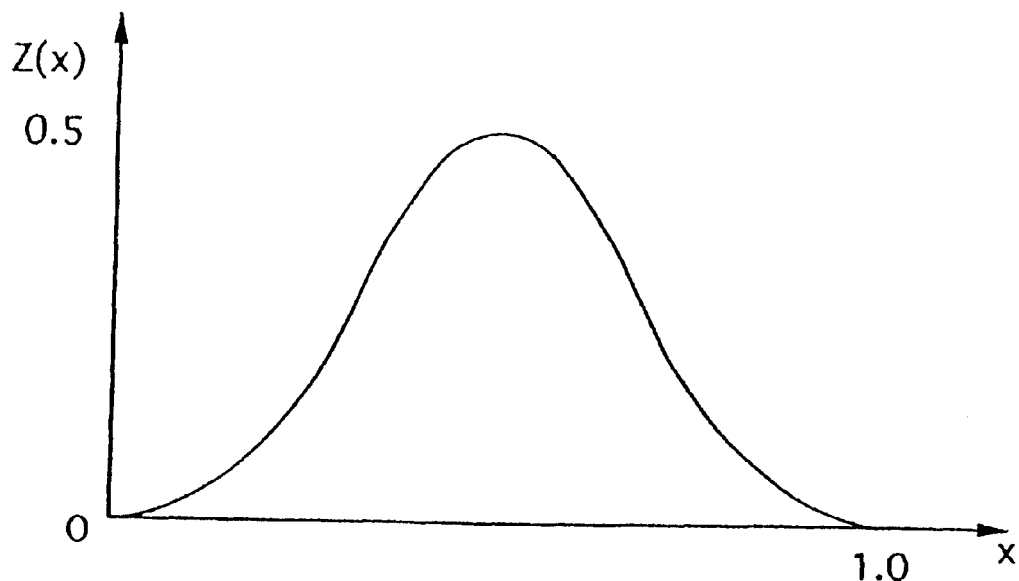
FIGS. 12($a$) and 12($b$) are diagrams showing convex mapping functions of, in which FIG. 12($a$) is a diagram showing a convex mapping function of a curve type
FIG. 12(b) is a diagram showing a convex mapping function of a linear type.
Figure 12B:
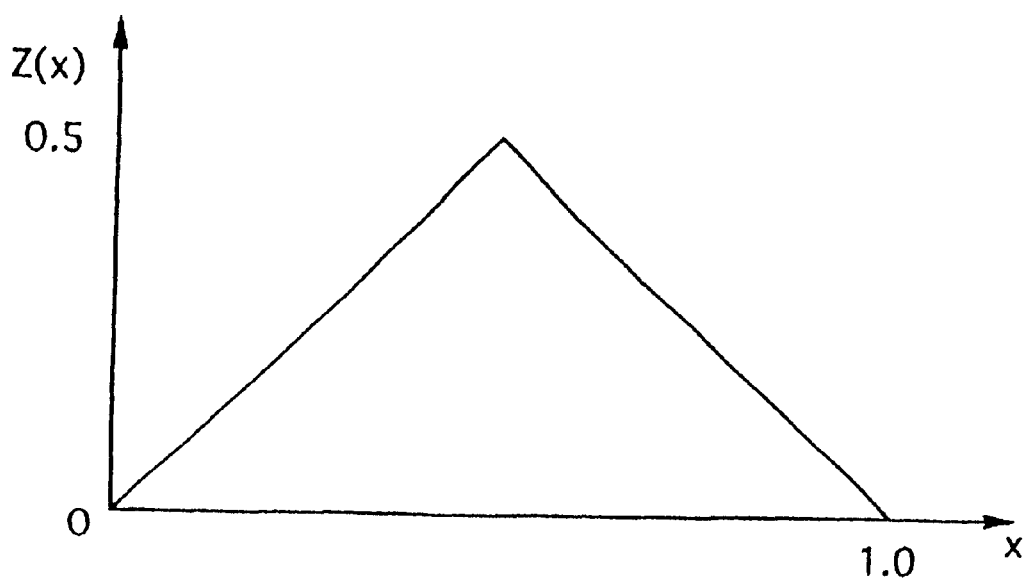

In Step 456, a function value $Z_{ab}$ is obtained using a mapping function of a dome type Z(x) (0≦x≦1, 0≦Z(x)≦0.5) as shown FIGS. 12(a) and 12(b) in order to disperse values of normalized distances d' to a proper extent.

$$Z_{ab}=Z(d')$$

After the function value $Z_{ab}$ is obtained in such a manner, new design variables $r_1'^a$, $r_1'^b$ are obtained by the following expressions in Step 458.

$$r_i'^a = r_i^a - \frac{\min(|r_i^a - B_L|, |r_i^a - Bu|)}{0.5} \cdot Z_{ab}$$

$$r_i'^b = r_i^b + \frac{\min(|r_i^b - B_L|, |r_i^a - Bu|)}{0.5} \cdot Z_{ab} \text{ or}$$

$$r_i'^a = r_i^a + \frac{\min(|r_i^a - B_L|, |r_i^a - Bu|)}{0.5} \cdot Z_{ab}$$

$$r_i'^b = r_i^b - \frac{\min(|r_i^b - B_L|, |r_i^a - Bu|)}{0.5} \cdot Z_{ab}$$

After $r_1'^a$, $r_1'^b$ are obtained in such a manner, in Step 460 design variable vectors $Vr'^a$, $Vr'^b$, which are lists of the new design variables, are obtained in the following way.

Figure 13A:
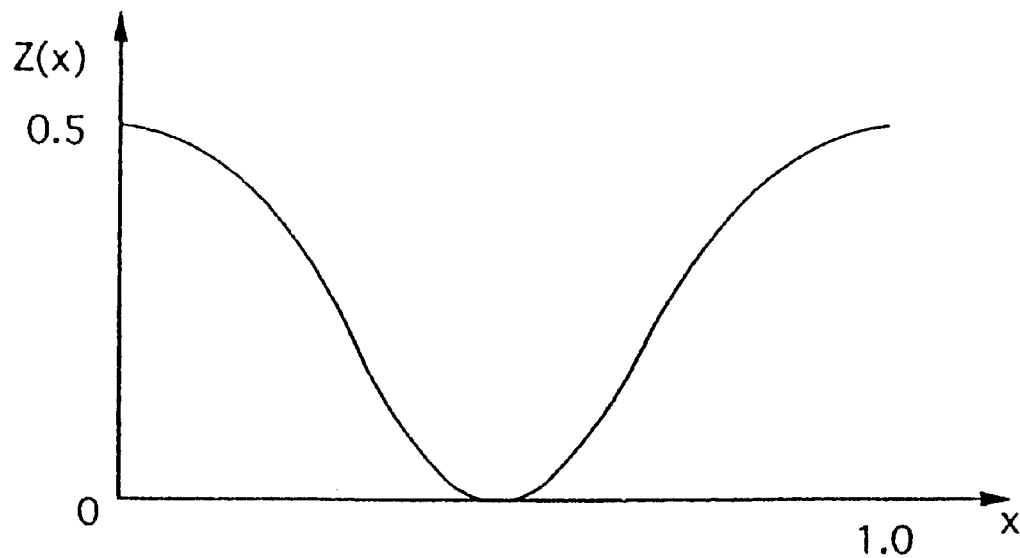
Figure 13B:
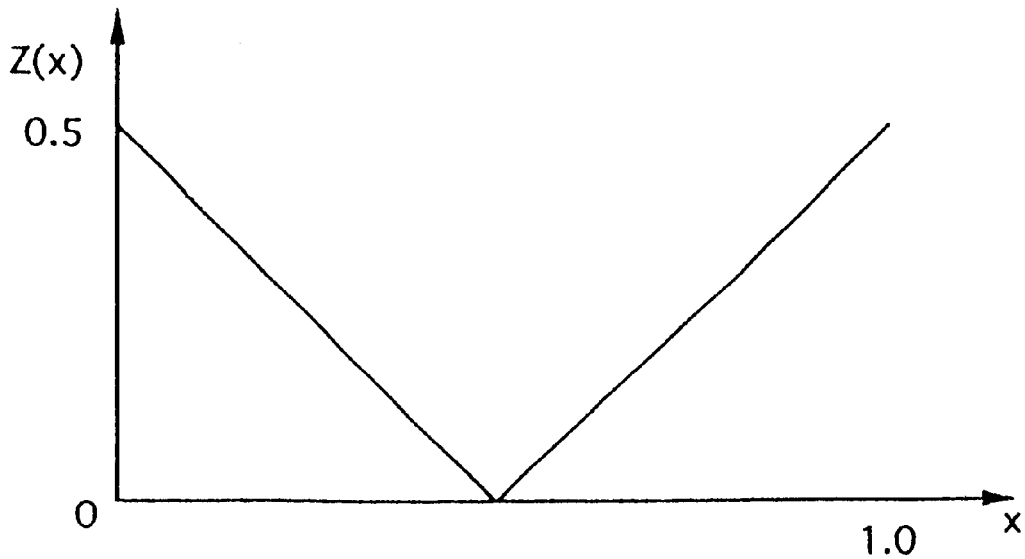

Meanwhile, the minimum and maximum values $B_L$ and $B_U$ in a range in which $r_i$ can be set are previously inputted by an operator. A mapping function Z(x) may be a mapping function of a valley type as shown in FIGS. 13(a), (b). In the above description, the number of a cross overing place i is only one, but a plurality of cross overing points, a uniform cross overing or the like may be employed, as shown in a book titled "Genetic Algorithm" compiled by Hiroaki Kitano.

After two new material models are produced in such a cross overing, in Step 416 of FIG. 10, it is determined whether or not mutation is made to occur at a probability S previously inputted by the operator. The mutation is to change a part of a design variable by a very small amount, which is performed in order to achieve a higher probability with which a population, which can be an optimum design variable, is included. In Step 416, if there is available a negative decision and mutation is not made to occur, the current two material models are kept intact in Step 426 and operation is advanced to Step 422. If a positive decision is available and mutation is made to occur, a mutation processing is effected in Step 420, as described below.

Figure 14:
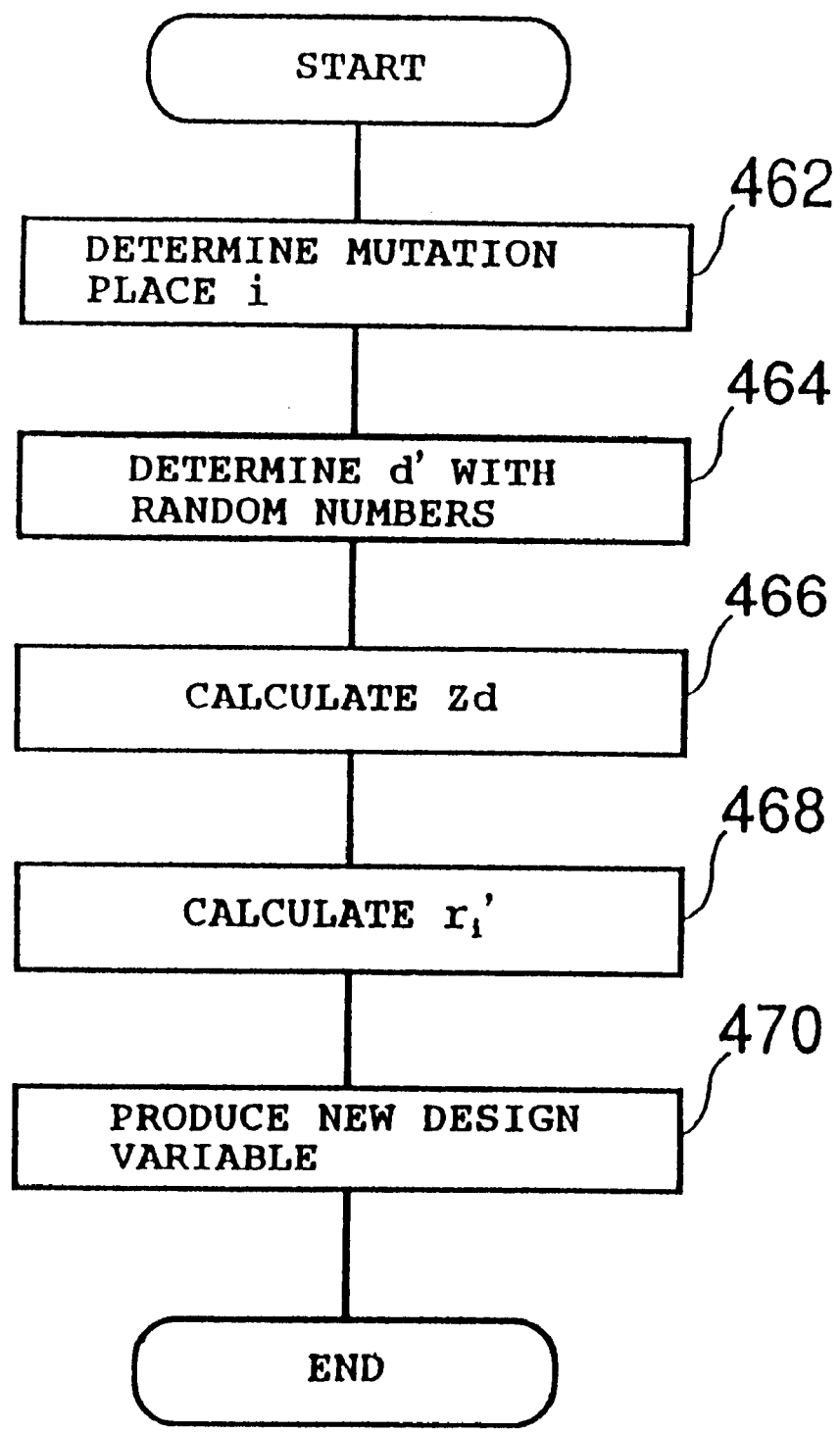
FIG. 14 is a flowchart showing a flow of a mutation process.

The mutation processing is performed by a mutation routine shown in FIG. 14. First of all, random numbers are produced in Step 462 and a place of mutation, i, is determined by use of the random numbers. In Step 464, the distance d' is determined by use of the random numbers in the following range:

$$0 \leq d' \leq 1$$

In Step 466, a mapping function of a dome type Z(x) (0≦x≦1, 0≦Z(x)≦0.5) as shown in FIGS. 12(a), (b) or a mapping function of a valley type Z(x) as shown in FIGS. 13(a), (b) is used and a function value Zd is obtained by the following expression.

$$Zd = Z(d')$$

After the function value Zd is obtained in such a manner, in Step 468 a new design variable $r_i'$ is obtained by the following equation.

$$r_i' = r_i - \frac{\min(|r_i - B_L|, |r_i - Bu|)}{0.5} \cdot Zd \text{ or}$$

$$r_i' = r_i + \frac{\min(|r_i - B_L|, |r_i - Bu|)}{0.5} \cdot Zd$$

After a design variable $r_i'$ is obtained in such a manner, a design variable vector Vr', which is a list of the new design variable, is obtained in Step 470 as in the following form:

$$Vr' = (r_1, r_2, \ldots r_i', r_{i+1}, \ldots r_{n-1})$$

In such a manner, values of an objective function and a constraint condition are calculated in Step 422 of FIG. 10 on the two new material models. In Step 424, an adaptive function is calculated from values of the objective function and the constraint condition by use of the expression (14) in a similar way to that of the above procedures.

In Step 426, the above mentioned two material models are stored. In Step 428, it is determined whether or not the number of material models stored in the Step 426 has reached the number N. When the number has not reached the number N, the Steps 408 to 428 are repeatedly executed until the number stored in the Step 425 reaches N. If the stored number has reached N, a decision of convergence is made in Step 430 but if not converged, the N material models are updated with stored material models in the Step 426 and the Steps 408 to 430 are repeatedly executed. If it is determined that convergence occurs in the Step 430, a design variable which makes the objective function the maximum, while roughly satisfying the constraint condition in the N material models, is adopted as a design variable which makes the objective function the maximum while roughly satisfying the constraint condition. In Step 432, a value of the design variable is used to determine a optimum composition point as is in the above embodiment, whereby the routine is terminated.

A decision of convergence in Step 430 is affirmatively made if any of the following conditions is satisfied, which are:

(1) the number of generations has reached M;
(2) the number of linear rows, in which a value of the first objective function is the largest, is equal to or more than q % of the whole; and
(3) the maximum value of an objective function is not updated in the following s generations, wherein M, q and s are previously inputted by the operator.

Tires were produced using rubber compounds having composition ratios of multi-component materials, wherein the ratios of components were obtained from the above mentioned embodiment and thus produced tires were subjected to various tests. In the following Table 1, components of multi-component materials are shown. In Table 2, compositional ratios by which the components of multi-component materials (rubber compounds) are contained, are shown.

TABLE 1

| | | Input | |
|---|---|---|---|
| | | Material | Design variable |
| 1 | Polymer A | | Natural rubber |
| 2 | Polymer B | | # 1500 (Nihon Gosei Gomu Co.) |
| 3 | Polymer C | | TO120 (Nihon Gosei Gomu Co.) |
| 4 | Carbon A | | Seast 7H (Tokai Carbon Co.) |
| 5 | Carbon B | | Seast 3 (Tokai Carbon Co.) |
| 6 | Silica A | | Nihon Silica Co., AQ silica |
| 7 | Oil A | | Aromatic oil |
| 8 | Chemical A | | Coupling agent (Degussa S169) |

TABLE 2

| | Design variable | Control | Composition 1 | Composition 2 |
|---|---|---|---|---|
| 1 | Natural rubber | 100 | — | 100 |
| 2 | #1500 | — | 41.25 | |
| 3 | TO120 | — | 96.25 | |
| 4 | Seast 7H | — | 50 | 25 |
| 5 | Seast 3 | 50 | — | — |
| 6 | AQ silica | — | — | 25 |
| 7 | Aromatic oil | 20 | — | 20 |
| 8 | Coupling agent | — | — | 2.5 |

Other components (a vulcanizing agent, vulcanization accelerator, antioxidant and the like) are properly contained.

In material optimization by the above mentioned embodiment, an objective function and a constraint condition are determined in the following way:

(Objective Function)

Composition 1: DRY$\mu$+Wet$\mu$ is maximized.

Composition 2: Wet$\mu$+Heat Generating Property is maximized.

(Constraint Condition)

A characteristic, which has no contribution to the objective function, is 95 or larger.

Tires were actually formed by rubber compounds according to compositional ratios of multi-component materials and obtained tires were subjected to various tests, which results are shown in Table 3 below:

TABLE 3

| | Destruction | Heat generation | Wear-out | Wet$\mu$ | Ice$\mu$ | DRY$\mu$ |
|---|---|---|---|---|---|---|
| Control | 100 | 100 | 100 | 100 | 100 | 100 |
| Composition 1 | 97 | 95 | 100 | 105 | 97 | 105 |
| Composition 2 | 95 | 105 | 100 | 110 | 100 | 99 |

The tests of the table 2 were measured in the following ways:

Destruction is to conduct a tensile test at room temperature (25° C.) in accordance to JIS K 6251, a tensile strength is measured when a specimen is broken down and respective index values normalized with a control being 100 are obtained on the compositions 1 and 2 and shown in the table, wherein it is understood that the larger a value in the table, the better the performance.

Heat generation is to conduct an impact resilience test at room temperature (25° C.) in accordance to JIS K 6255, an impact resilience is measured, an inverse number is calculated and then respective index values normalized with a control being 100 are obtained on the compositions 1 and 2 and shown in the table, wherein it is understood that the larger a value in the table, the better the performance.

Wear-out is to conduct a run-born test, an abrasion resistance index is measured at room temperature (25° C.) in accordance to JIS K 6264 and then respective index values normalized with a control being 100 are obtained on the compositions 1 and 2 and shown in the table, wherein it is understood that the larger a value in the table, the better the performance.

Wet$\mu$ shows a value of a brake test in a wet condition and the test is conducted in such a way that a test tire is mounted to an automobile, the automobile is driven to run on a wet road (test course), a brake is actuated by stepping down at a speed of 20 km/hr (forced braking) to lock the test tire, whereby a distance, which the automobile run until it stops, is measured. Then respective index values normalized with a control being 100 are obtained on the compositions 1 and 2 and shown in the table, wherein it is understood that the larger a value in the table, the better the performance.

Ice$\mu$ shows a value of a brake test in an icy condition and the test is conducted in such a way that a test tire is mounted to an automobile, the automobile is driven to run on an icy road (test course), a brake is actuated by stepping down at a speed of 40 km/hr (forced braking) to lock a tire, whereby a distance, which the automobile run until it stops, is measured. Then respective index values normalized with a control being 100 are obtained on the compositions 1 and 2 and shown in the table, wherein it is understood that the larger a value in the table, the better the performance.

DRY$\mu$ shows a value of a brake test in a dry condition and the test is conducted in such a way that a test tire is mounted to an automobile, the automobile is driven to run on a dry road (test course), a brake is actuated by stepping down at a speed of 60 km/hr (forced braking) to lock a tire, whereby a distance, which the automobile run until it stops, is measured. Then respective index values normalized with a control being 100 are obtained on the compositions 1 and 2 and shown in the table, wherein it is understood that the larger a value in the table, the better the performance.

INDUSTRIAL APPLICABILITY

As has been described above, a design method, an optimization analyzing apparatus and a storage medium having a stored optimization analyzing program, for a multi-component material according to the present invention relates to a design method for material design for a multi-component material composed of a plurality of components, for example a multi-component material applicable to a composition design, an optimization analyzing apparatus and a storage medium having a stored optimization program for a multi-component material. The design method, apparatus and medium of the present invention is preferably used for a composition design of a multi-component material, such as a composition composed of a plurality of components, for example a composition design of a rubber compound such as a rubber for a tire, and especially it is preferable to be used for a design when a correlation between mechanical behaviors which contributes to performance and compositional ratios is non-linear.

What is claimed is:

1. A design method for a multi-component material comprising the steps of:
   (a) determining a conversion system using learning in which a non-linear correspondence between compositional ratios of multi-component materials composed of a plurality of components as inputs and mechanical behaviors of the multi-component materials as outputs is established;
   (b) determining an objective function expressing said mechanical behaviors and setting a constraint condition constraining the allowable range of at least one of said mechanical behaviors and said compositional ratios of the multi-component materials; and
   (c) determining a compositional ratio of the multi-component materials which gives an optimal solution of an objective function by using said objective function and said constraint condition on the basis of the conversion system determined in said step (a) to design the multi-component materials on the basis of the compositional ratio which gives the optimal solution of the objective function.

2. The design method for a multi-component material according to claim 1, wherein said step (c) comprises the steps of: defining the compositional ratios of the multi-component materials as a design variable; obtaining a value of the design variable, which gives an optimal solution of the objective function on the basis of the conversion system determined in said step (a) while considering the constraint condition; and designing the multi-component materials by using the design variable which gives the optimal solution of the objective function.

3. The design method for a multi-component material according to claim 2, wherein the step (c) comprises:
   predicting a change in the design variable which gives the optimal solution of the objective function while considering the constraint condition based on a sensitivity of the objective function which is a ratio of a changed quantity of the objective function to a unit changed quantity of the design variable and a sensitivity of the constraint condition which is a ratio of a changed quantity of the constraint condition to a unit changed quantity in the design variable;
   calculating a value of the objective function when the design variable is changed in a corresponding manner to a predicted quantity and a value of the constraint condition when the design variable is changed in a corresponding manner to a predicted quantity; and
   obtaining a value of the design variable which gives an optimal solution of the objective function using the conversion system determined in said step (a) based on the predicted and calculated values while considering the constraint condition.

4. The design method for a multi-component material according to claim 1, wherein said step (c) comprises the steps of:
   (d) selecting as a design variable one compositional ratio of the compositional ratios of the multi-component materials included in the conversion system determined in said step (a);
   (e) changing a value of the design variable selected in the conversion system determined in said step (a) until the optimal solution of the objective function is given using the conversion system determined in said step (a) while considering said constraint condition; and
   (f) designing the multi-component material based on the compositional ratio of the multi-component materials at the design variable which gives the optimal solution of the objective function.

5. The design method for a multi-component material according to claim 4, wherein in said step (b) comprising a step of determining a constraint condition, constraining an allowable range of at least one of the mechanical behaviors other than said determined objective function and the compositional ratios of said multi-component materials.

6. The design method for a multi-component material according to claim 4, wherein said step (e) comprises:
- predicting a change in the design variable which gives the optimal solution of the objective function while considering the constraint condition based on a sensitivity of the objective function which is a ratio of a changed quantity of the objective function to a unit change quantity of the design variable and a sensitivity of the constraint condition which is a ratio of a changed quantity of the constraint condition to a unit change quantity of the design variable;
- calculating a value of the objective function when the design variable is changed in a corresponding manner to a predicted quantity and a value of the constraint conditions when the design variables are changed in a corresponding manner to a predicted quantity; and
- changing a value of the design variable on the basis of the conversion system determined in said step (a) based on said predicted and calculated values while considering the constraint condition, until the selected value of the design variable gives the optimal solution of the objective function.

7. The design method for a multi-component material according to claim 1, wherein said step (c) comprises the steps of: defining the compositional ratios of the multi-component materials in the conversion system determined in said step (a) as material base models to determine groups for selection comprising a plurality of material base models; determining the objective function, a design variable, the constraint condition and an adaptive function which can be evaluated from the objective function for material base models of the groups for selection; selecting two material base models from the groups for selection; effecting at least one of producing new material base models by cross overing the design variables of the two material base models, at a predetermined probability with each other and producing new material bases model by modifying in part the design variables of at least one of the two material base models; obtaining an objective function, a constraint condition and an adaptive function of the new material base models which has been produced using the conversion system determined in said step (a) by changing the design variable of the new material base models; storing the material base models whose design variables have been changed and the material base models whose design variables have not been changed; repeating the storing steps until the number of the stored material base models reaches a predetermined number; determining whether or not new groups comprising the stored material base models of the predetermined number satisfy a predetermined convergence condition; wherein if not, the new groups are defined as the groups for selection and the above steps are repeated until the new groups satisfy the predetermined convergence condition; and if the predetermined convergence condition is satisfied, designing a multi-component material based on the compositional ratio of the multi-component materials obtained by the design variable of one of predetermined number of the stored material base models which gives an optimal solution of the objective function on the basis of the conversion system determined in said step (a) while considering the constraint condition.

8. The design method for a multi-component material according to claim 1, wherein in said step (a) said conversion system is constructed with data in a multi-layered feed forward type neural network which has learned so as to convert the compositional ratios of the multi-component materials to the mechanical behaviors thereof.

9. A rubber compound which is formed in composition having the compositional ratio of multi-component materials designed by a design method of a multi-component material comprising the steps of:
- (a) determining a conversion system using learning in which a non-linear correspondence between compositional ratios of multi-component materials composed of a plurality of components as inputs and mechanical behaviors of the multi-component materials as outputs is established;
- (b) determining an objective function expressing said mechanical behaviors and setting a constraint condition constraining the allowable range of at least one of said mechanical behaviors and said compositional ratios of the multi-component materials; and
- (c) determining a compositional ratio of the multi-component materials which gives an optimal solution of an objective function by using said objective function and said constraint condition on the basis of the conversion system determined in said step (a) to design the multi-component materials on the basis of the compositional ratio which gives the optimal solution of the objective function.

10. An optimization analyzing apparatus comprising;
- conversion system calculating means using learning for determining a non-linear corresponding relation between compositional ratios of multi-component materials composed of a plurality of components as inputs and mechanical behaviors of the multi-component materials as outputs;
- input means for inputting an objective function and constraint condition as optimization items by determining the objective function expressing the mechanical behaviors and determining the constraint condition which constrains an allowable range of at least one of the mechanical behaviors and the compositional ratios of the multi-component materials; and
- optimization calculation means for determining a compositional ratio of the multi-component materials which gives an optimal solution of the objective function by using the optimization item inputted by the input means on the basis of said conversion system calculation means.

11. The optimization analyzing apparatus according to claim 10, wherein a non-linear corresponding relation between, on the one hand, the compositional ratios of said multi-component materials and a condition to be applied to the multi-component materials and, on the other hand, the mechanical behaviors of the multi-component materials is obtained by said conversion system calculation means.

12. The optimization analyzing apparatus according to claim 10, wherein said optimization calculation means comprises: selecting means for selecting one compositional ratio of the compositional ratios of the multi-component materials included in said conversion system calculation means as the design variable; change means for changing a value of the design variable selected from said conversion calculation means until the value of the objective function is given the optimal solution, while considering the constraint condition; optimal solution calculation means for calculating a value of the design variable until the objective function is given the optimal solution on the basis of the conversion system calculation means; and design means for designing a multi-component material based on the compositional ratio at the design variable which gives the optimal solution of the objective function.

13. The designing apparatus for a multi-component material according to claim 10, comprising; defining the compositional ratios of the multi-component materials in a conversion system determined in said conversion system calculation means as material base models to determine groups for selection composed of a plurality of material base models; determining the objective function, a design variable, a constraint condition and an adaptive function which can be evaluated from the objective function, for material base models in the groups for selection; selecting two material base models from the groups for selection; effecting at least one of producing new material base models by cross overing the design variables of the two material base models, at a predetermined probability with each other and producing new material base models by modifying in part the design variables of at least one of the two material base models; obtaining an objective function, a constraint condition and an adaptive function of the new material base models which have been produced using the conversion system determined in said conversion calculation means by changing the design variable; storing the material base models whose design variable have been changed and material base models whose design variables have not been changed; repeating the storing steps until the number of the stored material base models reaches a predetermined number; determining whether or not new groups comprising the stored material base models of the predetermined number satisfy a predetermined convergence condition; wherein if not, the new groups are defined as the groups for selection and the above steps are repeating until the group for selection satisfies the predetermined convergence condition; and if the predetermined convergence condition is satisfied, designing a multi-component material based on the compositional ratio of the multi-component materials at the design variable of one of the predetermined number of the stored material base models which gives an optimal solution of the objective function, on the basis of the conversion system determined in said conversion system calculation means, while considering the constraint condition.

14. The optimization analyzing apparatus according to claim 10 wherein said conversion system calculation means comprises a multi-layered feed forward type neural network which has learned so as to convert the compositional ratios of the multi-component materials to the mechanical behaviors thereof.

15. A computer-readable storage medium having a stored optimization analyzing program for designing a multi-component material by a computer in which the optimization analyzing program is programmed, said stored optimization analyzing program performing the steps of:

using learning, determining a non-linear corresponding relation between compositional ratios of multi-component materials as inputs and mechanical behaviors of the multi-component materials as outputs;

determining an objective function expressing the mechanical behaviors;

determining a constraint condition constraining an allowable range of at least one of the mechanical behaviors and the compositional ratios of the multi-component materials; and obtaining the compositional ratio of the multi-component materials which gives an optimal solution of the objective function, based on the determined corresponding relation, the objective function and the constraint condition to design a multi-component material on the basis of the compositional ratio of the multi-component materials which gives the optimal solution of the objective function.

16. The storage medium having a stored optimization analyzing program designing a multi-component material according to claim 15, wherein a design of a multi-component material on the basis of a compositional ratio of the multi-component materials comprises; selecting as a design variable one of the compositional ratios of the multi-component material included in the determined corresponding relation based on the determined corresponding relation, the objective function, and the constraint condition; changing a value of the design variable selected from the determined corresponding relation until the objective function is given the optimal solution while considering the constraint condition;

designing the multi-component material, based on the compositional ratio of the multi-component materials obtained by the design variable which gives the optimal solution to the objective function.

17. The storage medium having a stored optimization analyzing program for designing a multi-component material according to claim 16, wherein the constraint condition constrains an allowable range of at least one of the mechanical behaviors other than the determined objective function and the compositional ratios of the multi-component materials.

18. The storage medium having a stored optimization analyzing program for design of a multi-component material according to claim 16, wherein the change of the design variable is effected by predicting a change quantity of the design variable which gives the optimal solution to the objective function while considering the constraint condition based on a sensitivity of the objective function which is a ratio of a changed quantity of the objective function to a unit change quantity of the design variable and a sensitivity of the constraint condition which is a ratio of a changed quantity of the constraint condition to a unit change quantity of the design variable; calculating a value of the objective function when the design variable is changed in a corresponding manner to a predicted quantity and a value of the constraint condition when the design variable is changed in a corresponding manner to a predicted quantity; and changing a value of the design variable to be selected, by using the predicted and calculated values while considering said constraint condition until the objective function is given the optimal solution.

19. The storage medium having a stored optimization analyzing program for designing a multi-component material according to claim 16; wherein the design of a multi-component material based on a compositional ratio comprises said stored optimization analyzing program performing the following steps:

defining the compositional ratios of the multi-component materials in the determined corresponding relation as material base models to determine groups for selection composed of a plurality of material base models;

determining the objective function, a design variable, a constraint condition and an adaptive function which can be evaluated from the objective function for material base models in the groups for selection;

selecting two material base models from the group for selection; effecting at least one of producing new material base models by cross overing the design variables of the two material base models at a predetermined probability with each other, and producing new material base models by modifying in part the design variables of one of the two material base models;

obtaining an objective function, a constrained condition and an adaptive function of the material base models whose design variables have been changed;

storing the material base model whose design variable has been changed and the material base models whose design variables have not been changed;

repeating the storing step until the number of the stored material base models reaches a predetermined number;

determining whether or not new groups comprising the stored material base models of the predetermined number satisfy a predetermined convergence condition; wherein if not the new groups are defined as the groups for selection and the above steps are repeated until the new groups satisfy the predetermined convergence condition; and if the predetermined convergence condition is satisfied, designing a multi-component material, based on the compositional ratio of the multi-component materials obtained by the design variable of one of the predetermined number of the stored material base models which gives the optimal solution of the objective function, on the basis of said corresponding relation while considering the constraint condition.

* * * * *